(12) United States Patent
Nakamura et al.

(10) Patent No.: US 8,846,823 B2
(45) Date of Patent: Sep. 30, 2014

(54) WATER ABSORBING AGENT AND PRODUCTION METHOD THEREOF

(75) Inventors: Masatoshi Nakamura, Himeji (JP); Koji Miyake, Okayama (JP); Hirofumi Shibata, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 2100 days.

(21) Appl. No.: 11/579,603

(22) PCT Filed: Apr. 28, 2005

(86) PCT No.: PCT/JP2005/008577
§ 371 (c)(1),
(2), (4) Date: Nov. 3, 2006

(87) PCT Pub. No.: WO2005/108472
PCT Pub. Date: Nov. 17, 2005

(65) Prior Publication Data
US 2008/0032888 A1    Feb. 7, 2008

(30) Foreign Application Priority Data

May 7, 2004 (JP) .................................. 2004-138866

(51) Int. Cl.
*C08F 283/00* (2006.01)
*A61L 15/60* (2006.01)
*C08J 3/24* (2006.01)

(52) U.S. Cl.
CPC ............... *C08J 3/245* (2013.01); *A61L 15/60* (2013.01); *C08J 2300/14* (2013.01)
USPC ............................. 525/418; 525/379; 502/402

(58) Field of Classification Search
USPC ............... 502/401, 402, 439, 526; 525/330.1, 525/330.2, 379, 418; 604/372; 264/140, 264/40.4; 424/409, 411, 78.08–78.37; 510/136, 158, 119; 524/442, 445; 523/11

See application file for complete search history.

(56) References Cited

U.S. PATENT DOCUMENTS 3,935,099 A    1/1976  Weaver et al.
3,959,568 A    5/1976  Hill, Jr. et al.
(Continued)

FOREIGN PATENT DOCUMENTS

CA    2426514    3/2003
EP    0456136    11/1991
(Continued)

OTHER PUBLICATIONS

Japanese Office Action dated Mar. 29, 2011 issued for Japanese Application No. 2005-127818.
(Continued)

*Primary Examiner* — Kaj K Olsen
*Assistant Examiner* — Pritesh Darji
(74) *Attorney, Agent, or Firm* — Harness, Dickey & Pierce, P.L.C.

(57) ABSTRACT

A water absorbing agent and a method for producing the water absorbing agent are disclosed. Water absorbent resin particles having an internal cross-linked structure obtained by polymerizing a water-soluble unsaturated monomer, organic acid, and water-soluble multivalent metal salt are mixed, so that it is possible to provide a water absorbing agent which suppresses permeation of metal components into the water absorbent resin particles and enables the metal components to evenly adhere to an entire surface of the water absorbent resin in a dot manner.

12 Claims, 1 Drawing Sheet

(56) References Cited

U.S. PATENT DOCUMENTS

| | | | |
|---|---|---|---|
| 4,076,663 A | 2/1978 | Masuda et al. | |
| 4,090,013 A | 5/1978 | Ganslaw et al. | |
| 4,093,776 A | 6/1978 | Aoki et al. | |
| 4,124,748 A | 11/1978 | Fujimoto et al. | |
| 4,367,323 A | 1/1983 | Kitamura et al. | |
| 4,389,513 A | 6/1983 | Miyazaki | |
| 4,446,261 A | 5/1984 | Yamasaki et al. | |
| 4,625,001 A | 11/1986 | Tsubakimoto et al. | |
| 4,654,039 A | 3/1987 | Brandt et al. | |
| 4,683,274 A | 7/1987 | Nakamura et al. | |
| 4,690,996 A | 9/1987 | Shih et al. | |
| 4,693,713 A | 9/1987 | Chmelir et al. | |
| 4,721,647 A | 1/1988 | Nakanishi et al. | |
| 4,738,867 A | 4/1988 | Itoh et al. | |
| 4,748,076 A | 5/1988 | Saotome | |
| 4,769,427 A | 9/1988 | Nowakowsky et al. | |
| 4,771,105 A | 9/1988 | Shirai et al. | |
| 4,873,299 A | 10/1989 | Nowakowsky et al. | |
| 4,950,692 A | 8/1990 | Lewis et al. | |
| RE33,839 E | 3/1992 | Chmelir et al. | |
| 5,250,640 A | 10/1993 | Irie et al. | |
| 5,264,495 A | 11/1993 | Irie et al. | |
| 5,275,773 A | 1/1994 | Irie et al. | |
| 5,300,192 A | 4/1994 | Hansen et al. | |
| 5,308,896 A | 5/1994 | Hansen et al. | |
| 5,322,896 A | 6/1994 | Ueda et al. | |
| 5,447,977 A | 9/1995 | Hansen et al. | |
| 5,478,879 A | 12/1995 | Kajikawa et al. | |
| 5,538,783 A | 7/1996 | Hansen et al. | |
| 5,543,215 A | 8/1996 | Hansen et al. | |
| 5,571,618 A | 11/1996 | Hansen et al. | |
| 5,589,256 A | 12/1996 | Hansen et al. | |
| 5,609,727 A | 3/1997 | Hansen et al. | |
| 5,610,208 A | 3/1997 | Dairoku et al. | |
| 5,614,570 A | 3/1997 | Hansen et al. | |
| 5,843,575 A | 12/1998 | Wang et al. | |
| 5,849,405 A | 12/1998 | Wang et al. | |
| 5,851,672 A | 12/1998 | Wang et al. | |
| 5,858,535 A | 1/1999 | Wang et al. | |
| 5,973,042 A * | 10/1999 | Yoshinaga et al. | 524/192 |
| 6,071,976 A | 6/2000 | Dairoku et al. | |
| 6,099,950 A | 8/2000 | Wang et al. | |
| 6,228,930 B1 | 5/2001 | Dairoku et al. | |
| 6,239,230 B1 | 5/2001 | Eckert et al. | |
| 6,300,275 B1 | 10/2001 | Weir | |
| 6,323,252 B1 | 11/2001 | Gartner et al. | |
| 6,376,618 B1 | 4/2002 | Mitchell et al. | |
| 6,414,214 B1 | 7/2002 | Engelhardt et al. | |
| 6,433,058 B1 | 8/2002 | Weir et al. | |
| 6,448,320 B1 | 9/2002 | Igarashi et al. | |
| 6,458,921 B1 | 10/2002 | Dairoku et al. | |
| 6,605,673 B1 | 8/2003 | Mertens et al. | |
| 6,620,889 B1 | 9/2003 | Mertens et al. | |
| 6,716,929 B2 | 4/2004 | Wilson | |
| 6,720,073 B2 | 4/2004 | Lange et al. | |
| 6,730,387 B2 | 5/2004 | Rezai et al. | |
| 6,831,142 B2 | 12/2004 | Mertens et al. | |
| 6,992,144 B2 | 1/2006 | Dairoku et al. | |
| 2002/0013394 A1 | 1/2002 | Dairoku et al. | |
| 2002/0128618 A1 | 9/2002 | Frenz et al. | |
| 2002/0165288 A1 | 11/2002 | Frenz et al. | |
| 2002/0169252 A1 | 11/2002 | Wilson | |
| 2002/0193492 A1 | 12/2002 | Wilson | |
| 2003/0020199 A1* | 1/2003 | Kajikawa et al. | 264/140 |
| 2003/0060112 A1 | 3/2003 | Rezai et al. | |
| 2003/0069359 A1 | 4/2003 | Torii et al. | |
| 2003/0087983 A1 | 5/2003 | Kajikawa et al. | |
| 2003/0092849 A1* | 5/2003 | Dairoku et al. | 525/329.7 |
| 2003/0207997 A1 | 11/2003 | Mertens et al. | |
| 2004/0019342 A1 | 1/2004 | Nagasuna et al. | |
| 2004/0071966 A1 | 4/2004 | Inger et al. | |
| 2004/0106745 A1 | 6/2004 | Nakashima et al. | |
| 2005/0020780 A1 | 1/2005 | Inger et al. | |
| 2005/0070671 A1 | 3/2005 | Torii et al. | |
| 2005/0221980 A1 | 10/2005 | Adachi et al. | |
| 2006/0025536 A1 | 2/2006 | Dairoku et al. | |
| 2006/0073969 A1 | 4/2006 | Torii et al. | |
| 2006/0204755 A1 | 9/2006 | Torii et al. | |
| 2006/0229413 A1 | 10/2006 | Torii et al. | |

FOREIGN PATENT DOCUMENTS

| | | |
|---|---|---|
| EP | 0530517 | 3/1993 |
| EP | 603292 | 6/1994 |
| EP | 0621041 | 10/1994 |
| EP | 0621041 A | 10/1994 |
| EP | 0668080 | 8/1995 |
| EP | 0844270 | 5/1998 |
| EP | 1178059 | 2/2002 |
| EP | 1191051 A2 | 3/2002 |
| EP | 1315770 | 5/2003 |
| EP | 1422257 A1 | 5/2004 |
| EP | 1516884 | 3/2005 |
| EP | 1516884 A | 3/2005 |
| EP | 1315770 | 8/2006 |
| JP | 58-501107 A | 7/1983 |
| JP | 61-46241 | 3/1986 |
| JP | 62-007745 | 1/1987 |
| JP | 64-56707 | 3/1989 |
| JP | 07-228788 | 8/1995 |
| JP | 9-124879 | 5/1997 |
| JP | 9-235378 | 9/1997 |
| JP | 9-509591 | 9/1997 |
| JP | 9-290000 | 11/1997 |
| JP | 63-270741 | 11/1998 |
| JP | 2000-327926 | 11/2000 |
| JP | 2001-96151 | 4/2001 |
| JP | 2001-224959 | 8/2001 |
| JP | 2002-241627 A | 8/2002 |
| JP | 2003-062460 | 3/2003 |
| JP | 2003-105092 | 4/2003 |
| JP | 2004-001355 A | 1/2004 |
| WO | WO 93/05080 | 3/1993 |
| WO | WO 95/05856 | 3/1995 |
| WO | WO-95/26209 A1 | 10/1995 |
| WO | WO 01/74913 | 10/2001 |
| WO | WO-03/004550 A1 | 1/2003 |
| WO | WO 2004/113452 | 12/2004 |

OTHER PUBLICATIONS

Japanese Office Action dated Dec. 7, 2010 for corresponding Japanese Application No. 2005-127818.
Chinese Office Action dated Dec. 23, 2013 issued in Chinese Application No. 201210313591.9.
Affidavit, Dr. Christian Speyerer, pp. 1-3.
Buchholz, F.L., et al. (1997) "Modern superabsorbent polymer technology", Wiley-VCH, pp. 149-153.
Buchholz, F.L., et al. (1997) "Modern superabsorbent polymer technology", Wiley-VCH, pp. 178.
Buchholz, F.L., et al. (1997) "Modern superabsorbent polymer technology", Wiley-VCH, pp. 192-221.
Decision rejecting the opposition dated Jun. 24, 2014 issued in EP Application No. 04746711.3.
Delivery Note No. 89077237 dated May 19, 1999.
Delivery Note No. 89097648 dated Aug. 24, 1999.
Statement of Delivery No. 89055427 dated Feb. 10, 1999—with English Translation.
Statement of Delivery No. 89055472 dated Feb. 10, 1999—with English Translation.
Summons to attend oral proceedings dated Jun. 10, 2014 issued in EP Application No. 04773399.3.

* cited by examiner

WATER ABSORBING AGENT AND PRODUCTION METHOD THEREOF

TECHNICAL FIELD

The present invention relates to (i) a water absorbing agent favorably used in sanitary materials such as disposable diapers, sanitary napkins, and so-called incontinence pads, and the like, and (ii) a production method of the water absorbing agent.

BACKGROUND ART

An absorbent core containing a hydrophilic fiber such as pulp and a water absorbent resin as its components is widely used in sanitary materials such as disposable diapers, sanitary napkins, incontinence pads and the like, in order to absorb body fluids.

Recently, the sanitary material such as the sanitary napkin and the like has higher performance and a thinner size, and an amount of the water absorbent resin used for each sanitary material tends to increase, and also a ratio of the water absorbent resin tends to increase with respect to the whole absorbent core constituted of the water absorbent resin and a hydrophilic fiber. That is, by using (i) a smaller amount of a hydrophilic fiber whose bulk density is low and (ii) a larger amount of a water absorbent resin having a superior water absorbing property and high bulk density, a ratio of the water absorbent resin contained in the absorbent core is increased, thereby making the sanitary material thinner without decreasing an amount of water absorption.

However, the sanitary material which includes a smaller amount of the hydrophilic fiber and a larger amount of the water absorbent resin is preferable merely in terms of liquid storage, but raises problems in terms of distribution and diffusion of liquid in actual use in diapers. For example, when a large amount of the water absorbent resin is used, the water absorbent resin becomes soft and gelatinous upon absorbing water. This causes a gel blocking phenomenon. As a result, a liquid diffusing property of the diaper significantly drops. In order to avoid such phenomenon and to keep high absorbing property of the absorbent core, a ratio of the hydrophilic fiber and the water absorbent resin is inevitably limited, so that there is a limit in making the sanitary material thinner.

As means for obtaining a water absorbent resin which is superior in liquid permeability and liquid diffusing property while preventing the gel blocking, a technique in which a metal component (metal salt, metal cation, or the like) is added to the water absorbent resin is known (for example, see Japanese Unexamined Patent Publication No. 7745/1987 (Tokukaisho 62-7745), Japanese Unexamined Patent Publication No. 270741/1988 (Tokukaisho 63-270741), Japanese Unexamined Patent Publication No. 124879/1997 (Tokukaihei 9-124879), U.S. Pat. No. 6,323,252, and International Publication No. 01/74913 pamphlet).

According to such a technique, a metal component (metal salt, metal cation, or the like) is added as an aqueous solution, so that a metal component permeates the water absorbent resin. Thus, it is impossible to sufficiently improve the liquid, permeability and liquid diffusing property so as to correspond to an amount of the metal component added. Further, the metal components permeate the water absorbent resin, so that an absorbency without load and an absorbency against pressure drop. Moreover, according to such a technique, the metal components unevenly adhere to a surface of the water absorbent resin in a plane manner, so that there is a problem in terms of expression of even properties.

DISCLOSURE OF INVENTION

An object of the present invention is to provide a method for producing a water absorbing agent by mixing metal components (metal salt, metal cation, or the like) with water absorbent resin particles, the method suppressing permeation of metal components into the water absorbent resin particles and enabling the metal components to evenly adhere to a whole surface of the water absorbent resin in a dot manner.

The inventors of the present invention diligently studied solutions of the foregoing problems. As a result, they found and confirmed that it is possible to solve all the foregoing problems by mixing water absorbent resin particles, organic acid (or salt thereof), and water-soluble multivalent metal salt, preferably by adding water-soluble multivalent metal salt and organic acid (or salt thereof) to water absorbent resin particles, thereby completing the present invention.

That is, a method according to the present invention for producing a water absorbing agent is characterized by comprising the step of mixing (i) water absorbent resin particles having an internal cross-linked structure obtained by polymerizing a water-soluble unsaturated monomer, (ii) organic acid (or salt thereof), and (iii) water-soluble multivalent metal salt.

Further, a water absorbing agent according to the present invention includes: water absorbent resin particles, including acrylic acid and/or a salt thereof as a constitutional unit, whose surfaces have been cross-linked by performing a heating treatment or using an organic cross-linking agent; organic acid (or salt thereof); and water-soluble multivalent metal salt.

For a fuller understanding of the nature and advantages of the invention, reference should be made to the ensuing detailed description taken in conjunction with the accompanying drawings.

BEST MODE FOR CARRYING OUT THE INVENTION

Figure 1:
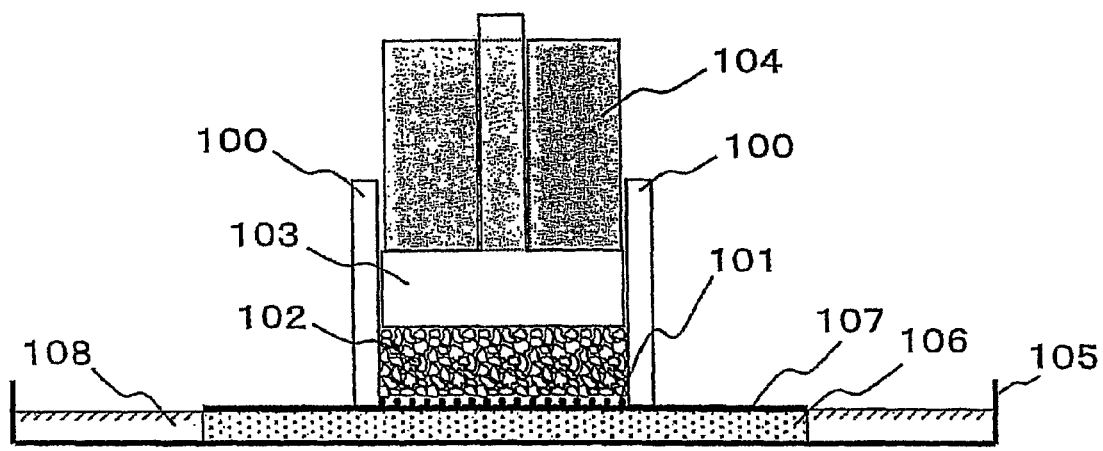
FIG. 1 schematically illustrates an arrangement of an apparatus for measuring AAP which is a value indicative of a performance of a water absorbing agent according to the present invention.

One embodiment of the present invention is described below. The scope of the present invention is not limited to the following embodiment, and the invention may be varied in other manner so as not depart from the spirit and scope of the invention.

[Water Absorbent Resin Particles]

The water absorbent resin particles used in the present invention are particles of a water-insoluble water-swelling hydrogel formation polymer (hereinafter, referred to also as a water absorbent resin) obtained by polymerizing a water-soluble unsaturated monomer, and are particles, each having a sphere shape or an irregular shape, whose absorption capacity with respect to a physiological saline (0.90 mass % of NaCl aqueous solution) is not less than 10. Note that, in the present invention, the water absorbent resin particles are referred to also as the water absorbent resin.

Specific examples of the water-insoluble water-swelling hydrogel formation polymer includes: a partially neutralized cross-linked polyacrylic acid polymer (U.S. Pat. No. 4,625, 001, U.S. Pat. No. 4,654,039, U.S. Pat. No. 5,250,640, U.S. Pat. No. 5,275,773, European Patent No. 456136, and the like); a cross-linked partially neutralized starch-acrylic acid graft polymer (U.S. Pat. No. 4,076,663); an isobutylene-maleic acid copolymer (U.S. Pat. No. 4,389,513); a saponified vinyl acetate-acrylic acid copolymer (U.S. Pat. No. 4,124, 748); a hydrolyzed acrylamide (co)polymer (U.S. Pat. No. 3,959,569); a hydrolyzed acrylonitril copolymer (U.S. Pat. No. 3,935,099); and the like.

It is preferable that the water absorbent resin used in the present invention is particles of a water absorbent resin made of a cross-linked polyacrylic acid (or salt thereof) polymer, obtained by polymerizing a monomer containing acrylic acid and/or a salt thereof, which cross-linked polyacrylic acid (or salt thereof) polymer contains acrylic acid and/or a salt thereof as a constitutional unit. In the present invention, the cross-linked polyacrylic acid (or salt thereof) polymer is a cross-linked polymer obtained by polymerizing a monomer containing not less than 50 mol %, preferably not less than 70 mol %, more preferably not less than 90 mol % of acrylic acid and/or a salt thereof, with respect to all constitutional units. Further, it is preferable that 50 to 90 mol %, preferably 60 to 80 mol % of an acid group contained in the polymer is neutralized, and examples of the salt include: alkali metal salt such as sodium, potassium, and lithium; ammonium salt; and amine salt. The water absorbent resin for forming salt may be neutralized in a monomer phase before polymerization, or may be neutralized during and after polymerization, or these processes may be combined with each other.

The polyacrylic acid (or salt thereof) cross-linked polymer which serves as the water absorbent resin particles favorably used in the present invention may be obtained by copolymerizing a monomer (acrylic acid and/or a salt thereof) used as a main component with other monomer as required. Specific examples of other monomer include: an anionic unsaturated monomer such as methacrylic acid, maleic acid, vinyl sulfonic acid, styrene sulfonic acid, 2-(meth)acrylamide-2-methylpropane sulfonic acid, 2-(meth)acryloyloxyethane sulfonic acid, 2-(meth)acryloyloxypropane sulfonic acid, and salt thereof; a nonionic hydrophilic-group-containing unsaturated monomer such as acrylamide, methacrylamide, N-ethyl(meth)acrylamide, N-n-propyl(meth) acrylamide, N-isopropyl(meth)acrylamide, N,N-dimethyl(meth)acrylamide, 2-hydroxyethyl(meth)acrylate, 2-hydroxypropyl (meth)acrylate, methoxypolyethyleneglycol (meth)acrylate, polyethyleneglycol mono (meth)acrylate, vinylpyridine, N-vinylpyrrolidone, N-acryloylpiperidine, and N-acryloylpyrrolidine, and N-vinylacetamide; and cationic unsaturated monomer such as N,N-dimethylaminoethyl (meth)acrylate, N,N-diethylaminoethyl (meth)acrylate, N,N-dimethylaminopropyl (meth)acrylate, N,N-dimethylaminopropyl (meth)acrylamide, and quaternary salt thereof; and the like. An amount of the monomer other than acrylic acid and/or a salt thereof is 0 to 30 mol %, preferably 0 to 10 mol %, with respect to the whole monomer.

The water absorbent resin particles used in the present invention is a cross-linked polymer having an internal cross-linked structure.

Examples of a method for introducing a cross-linked structure into the water absorbent resin particles used in the present embodiment are as follows: self cross-linking is promoted without using a cross-linking agent; an internal cross-linking agent having two or more polymerizable unsaturated groups and/or two or more reactive groups is copolymerized or reacted with the water absorbent resin particles; and a similar method. It is preferable to copolymerize or react the internal cross-linking agent.

Examples of the internal cross-linking agent include: N,N'-methylenebis(meth)acrylamide, (poly)ethyleneglycol di(meth)acrylate, (poly)propyleneglycol di(meth)acrylate, trimethylolpropanetri(meth)acrylate, trimethylolpropanedi (meth)acrylate, glycerinetri(meth)acrylate, glycerineacrylatemethacrylate, ethyleneoxide denatured trimethylolpropanetri(meth)acrylate, pentaerythritoltetra(meth)acrylate, dipentaerythritolhexa(meth)acrylate, triallyl cyanurate, triallyl isocyanurate, triallyl phosphate, triallyl amine, poly (meth)allyloxyalkane, (poly)ethyleneglycol diglycidyl ether, glycerol diglycidyl ether, ethyleneglycol, polyethyleneglycol, propyleneglycol, glycerine, pentaerythritol, ethylenediamine, polyethyleneimine, glycidyl(meth)acrylate, and the like. These internal cross-linking agents may be used either independently or in a suitable combination of two or more kinds. When using one or more internal cross-linking agents, it is preferable that a compound including not less than two polymerizable unsaturated groups is used as the internal cross-linking agent, taking into account the absorption characteristics or other properties of the product water absorbent resin particles. An amount of internal cross-linking agent used is preferably 0.005 to 3 mol %, more preferably 0.01 to 1.5 mol %, with respect to a total number of moles of the whole monomer.

In the polymerization, it is possible to add (i) hydrophilic polymers such as a mixture of starch and cellulose, a derivative of starch and cellulose, polyvinyl alcohol, polyacrylic acid (or salt thereof), cross-linked polyacrylic acid (or salt thereof), and the like or (ii) a chain transfer agent such as hypophosphorous acid (or salt thereof).

In polymerizing the monomer containing acrylic acid and/or a salt thereof as main components so as to obtain the water absorbent resin used in the present embodiment, bulk polymerization, reversed suspension polymerization, or precipitation polymerization may be performed. However, in terms of (i) performance of the water absorbent resin particles and (ii) controllability of polymerization, a more preferable method of polymerization is aqueous polymerization performed under such condition that an aqueous solution of the monomer is used. Such polymerization method is recited for example in U.S. Pat. No. 4,625,001, U.S. Pat. No. 4,769,427, U.S. Pat. No. 4,873,299, U.S. Pat. No. 4,093,776, U.S. Pat. No. 4,367,323, U.S. Pat. No. 4,446,261, U.S. Pat. No. 4,683, 274, U.S. Pat. No. 4,690,996, U.S. Pat. No. 4,721,647, U.S. Pat. No. 4,738,867, U.S. Pat. No. 4,748,076, and European Patent No. 1178059.

In initiating the polymerization, it is possible to use: a radical polymerization initiator such as potassium persulfate, ammonium persulfate, sodium persulfate, t-butylhydroperoxide, hydrogen peroxide, 2,2'-azobis(2-amidino-propane) dihydrochloride; or an active energy ray such as an ultraviolet ray and an electron ray. Further, in case of using a radical polymerization initiator, redox polymerization may be carried out by using a reducer such as sodium sulfite, sodium bisulfate, ferrous sulfate, L-ascorbic acid, and the like, together. An amount of polymerization initiators used is preferably 0.001 to 2 mol %, more preferably 0.01 to 0.5 mol %, with respect to the whole monomer.

It is general that a particle shape of thus obtained water absorbent resin particle is an irregularly-pulverized shape, a sphere shape, a fibrous shape, a bar shape, a substantially sphere shape, or an oblate shape. The water absorbent resin particle used in the present invention is particulate. Thus, it is preferable to use an irregularly-pulverized particle obtained by pulverizing the polymer after performing the drying operation since this results in greater effect of the present invention.

It is preferable to cross-link a vicinity of surfaces of the water absorbent resin particles of the present invention.

The surface cross-linking treatment may be performed by using a surface cross-linking agent or may be performed in accordance with other known surface cross-linking treating method.

As the surface cross-linking agent which can be used in the surface cross-linking treatment, it is possible to use an organic surface cross-linking agent or a multivalent metal component which can react with a functional group of the water absorbent resin particles, particularly with a carboxyl group of the water absorbent resin particles, so as to form a cross-linked structure. Particularly, it is preferable to use, for example, the following organic surface cross-linking agents: polyhydric alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol; epoxy compounds such as ethyleneglycol diglycidyl ether, polyethyleneglycol diglycidyl ether, glycerol polyglycidyl ether, diglycerol polyglycidyl ether, polyglycerol polyglycidyl ether, propyleneglycol diglycidyl ether, polypropyleneglycol diglycidyl ether, and glycidol; multivalent amine compounds such as ethylenediamine, diethylenetriamine, triethylenetetramine, tetraethylenepentamine, pentaethylenehexamine, and polyethyleneimine, and inorganic salts or organic salts thereof (for example, azetidinium salt and the like); multivalent isocyanate compounds such as 2,4-tolylenediisocyanate, and hexamethylenediisocyanate; multivalent oxazoline compounds such as 1,2-ethylenebisoxazoline; carbonic acid derivatives such as urea, thiourea, guanidine, dicyandiamide, and 2-oxazolidinone; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxolan-2-one, 4-methyl-1,3-dioxolan-2-one, 4,6-dimethyl-1,3-dioxolan-2-one, and 1,3-dioxepan-2-one; haloepoxy compounds such as epichlorohydrin, epibromohydrin, and α-methylepichlorohydrin, and multivalent amine addition products thereof (for example, Kymene produced by Hercules: registered trademark); silane coupling agents such as γ-glycidoxypropyltrimethoxysilane and γ-aminopropyltriethoxysilane; and oxethane compounds such as 3-methyl-3-oxethane methanol, 3-ethyl-3-oxethane methanol, 3-butyl-3-oxethane methanol, 3-methyl-3-oxethane ethanol, 3-ethyl-3-oxethane ethanol, 3-butyl-3-oxethane ethanol, 3-chloromethyl-3-methyloxethane, 3-chloromethyl-3-ethyloxethane, and a multivalent oxethane compound; and the like. These surface cross-linking agents may be used either independently or in a suitable combination of two or more kinds. Among the cross-linking agents, the polyhydric alcohol is preferable since it is superior in terms of safety and it improves the hydrophilic property of the surfaces of the water absorbent resin particles. Further, the polyhydric alcohol is used, so that affinity between the surfaces of the water absorbent resin particles and the multivalent metallic particles is improved, and a synergy effect between a multivalent alcohol residue and surfaces of the multivalent metallic particles enables the multivalent metallic particles to more evenly exist on surfaces of the water absorbent resin particles in a dot manner (the multivalent metallic particles locally exist).

An amount of the surface cross-linking agent used is preferably 0.001 to 5 parts by mass with respect to 0.100 parts by mass of solid components of the water absorbent resin particles.

In mixing the surface cross-linking agent with the water absorbent resin particles, water may be used. An amount of water to be used is preferably over 0.5 parts by mass and not more than 10 parts by mass, more preferably 1 part by mass to 5 parts by mass, with respect to 100 parts by mass of solid components of the water absorbent resin particles.

In mixing the surface cross-linking agent and aqueous solution thereof, a hydrophilic organic solvent and a third substance may be used as a mixing coadjuvant.

Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly) ethyleneglycol; amides such as ε-caprolactam and N,N-dimethylformamide; sulfoxides such as dimethylsulfoxide; polyhydric alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol. An amount of the hydrophilic organic solvent varies depending on a type, a particle diameter, a moisture content, and the like of the water absorbent resin particles. However, the amount of the hydrophilic organic solvent is preferably 10 parts by mass or less, more preferably 0.1 part by mass to 5 parts by mass, with respect to 100 parts by mass of solid components of the water absorbent resin particles. Further, inorganic acid, organic acid, polyamino acid, etc. that are recited in European Patent No. 0668080 as a third substance may exist therein. Such mixing coadjuvant may act as a surface cross-linking agent, but it is preferable to use a substance which prevents a water absorbing performance of the water absorbent resin particles from dropping after performing the surface cross-linking treatment. Particularly, it is preferable to use a volatile alcohol whose boiling point is less than 150° C. since the volatile alcohol evaporates at the time of the surface cross-linking treatment so that there is no residue.

In order to evenly mix the water absorbent resin particles with the surface cross-linking agent, non-cross-linking water-soluble inorganic bases (preferably, alkali metal salt, ammonium salt, alkali metal hydride, and ammonia or hydride thereof) or non-reducing alkali metal salt pH buffer (preferably, bicarbonate, dihydrogen phosphate salt, hydrogen phosphate salt, and the like) may coexist in mixing the water absorbent resin particles with the surface cross-linking agent. An amount of these components varies depending on a type, a particle diameter, etc. of the water absorbent resin particles, but preferably ranges from 0.005 to 10 parts by mass, more preferably from 0.05 to 5 parts by mass, with respect to 100 parts by mass of solid components of the water absorbent resin particles.

Various methods can be adopted in mixing the water absorbent resin particles with the surface cross-linking agent, but the following mixing methods may be performed: the water absorbent resin particles are immersed in the hydrophilic organic solvent, and a surface cross-linking agent dissolved in water and/or the hydrophilic organic solvent as required is mixed; the surface cross-linking agent dissolved in the water and/or the hydrophilic solvent is sprayed or dropped directly to the water absorbent resin particles.

Generally, it is preferable that the water absorbent resin is subjected to a heating treatment so as to promote the cross-linking reaction after mixing the water absorbent resin particles with the surface cross-linking agent. Conditions of the heating treatment are as follows. A heating temperature preferably ranges from 40° C. to 250° C., more preferably from 150° C. to 250° C. In case where the heating temperature is less than 40° C., the absorbing property such as the absorbency against pressure may be insufficiently improved. In case where the heating temperature exceeds 250° C., the water absorbent resin particles deteriorate which causes various performances to drop, so that it is necessary to be careful. A heating time preferably ranges from one minute to two hours, more preferably from five minutes to one hour.

In case where the water absorbent resin particles of the present invention are obtained by performing the heating treatment, the heating treatment is performed for example as follows. As recited in European Patent No. 530517, European Patent No. 603292, International Publication No. 95/05856, the dried water absorbent resin particles are further heated.

A particle diameter and a particle distribution of the water absorbent resin particles used in the present invention are not particularly limited. However, it is preferable to use water absorbent resin particles, having a relatively small particle diameter, in which a large number of small-diameter particles exist. Such water absorbent resin particles remarkably improve the water absorbing performances such as a water absorption rate, a capillary absorption capacity, and the like.

In order to improve the performances such as the water absorption rate, the capillary absorption capacity, and the like, a mass average particle diameter of the water absorbent resin particles used in the present invention is preferably 500 µm or less, more preferably 400 µm or less. Further, a ratio of particles each having a particle diameter of less than 300 µm in the water absorbent resin particles is preferably 10 mass % or more, more preferably 30 mass % or more, still more preferably 50 mass % or more, with respect to the whole water absorbent resin particles. It is possible to favorably obtain the water absorbent resin particles each having such a particle diameter by pulverizing the water absorbent resin (particles) obtained by the aqueous solution polymerization or adjusting particle sizes after sieving the water absorbent resin particles. Further, water absorbent resin particles obtained by agglomerating fine powder of water absorbent resin particles whose particle diameter is 300 µm or less may be used, or water absorbent resin particles obtained by mixing part of agglomerated fine powder with irregular-shape pulverized particles obtained by pulverizing the water absorbent resin may be used. In case where part of agglomerated water absorbent resin particles is mixed, it is possible to obtain a water absorbing agent which is much superior in absorbing properties such as a water absorption rate, a capillary absorption capacity, and the like. An amount of the agglomerated fine powder mixed is preferably 5 mass % or more, more preferably 10 mass % or more, still more preferably 15 mass % or more.

As a method for producing the agglomerated fine powder, it is possible to adopt a known technique for reproducing fine powder. Examples of the technique are as follows: hot water and fine powder of the water absorbent resin particles are mixed with each other and thus obtained mixture is dried (U.S. Pat. No. 6,228,930); fine powder of the water absorbent resin particles is mixed with a monomer aqueous solution and thus obtained mixture is polymerized (U.S. Pat. No. 5,264,495); water is added to fine powder of the water absorbent resin particles and thus obtained mixture is agglomerated at not less than a specific surface pressure (European Patent No. 844270); fine powder of the water absorbent resin particles is sufficiently swollen so as to form a non-crystalline gel and thus obtained non-crystalline gel is dried and pulverized (U.S. Pat. No. 4,950,692); fine powder of the water absorbent resin particles is mixed with a polymerized gel (U.S. Pat. No. 5,478,879); and a similar technique is performed. Among them, it is preferable to adopt the method in which hot water and fine powder of the water absorbent resin particles are mixed with each other and thus obtained mixture is dried. Note that, a particle diameter is indicated by a sieve diameter by which particles are classified.

In the water absorbent resin particles of the present invention, a centrifuge retention capacity (CRC) is preferably 10 (g/g) or more, more preferably 20 (g/g) or more, still more preferably 25 (g/g) or more. An upper limit of the centrifuge retention capacity (CRC) is not particularly limited, but is preferably 50 (g/g) or less, more preferably 45 (g/g) or less, still more preferably 40 (g/g) or less. In case where the centrifuge retention capacity (CRC) is less than 10 (g/g), an amount of absorbed liquid is so small that the water absorbent resin particles are not suitable for use in a sanitary material such as a diaper. Further, in case where the centrifuge retention capacity (CRC) exceeds 50 (g/g), it may be impossible to obtain a water absorbing agent which is superior in liquid permeability.

In the water absorbent resin particles of the present invention, an absorbency against pressure (AAP) (pressure is 4.83 kPa) is preferably 18 g/g or more, more preferably 20 g/g or more, still more preferably 22 (g/g) or more. In case where the absorbent against pressure (AAP) (pressure is 4.83 kPa) is less than 18 g/g, it may be impossible to obtain a water absorbing agent which is superior in liquid permeability.

In the water absorbent resin particles of the present invention, a saline flow conductivity (SFC) is preferably $10 \times 10^{-7}$ $cm^3 \cdot s \cdot g^{-1}$ or more, more preferably $30 \times 10^{-7}$ $cm^3 \cdot s \cdot g^{-1}$ or more, further more preferably $50 \times 10^{-7}$ $cm^3 \cdot s \cdot g^{-1}$ or more. In case where the saline flow conductivity (SFC) is less than $10 \times 10^{-7}$ $cm^3 \cdot s \cdot g^{-1}$, even when water-soluble multivalent metal salt is added, the liquid permeability may be unimproved.

In the water absorbent resin particles of the present invention, an amount of water-soluble components is preferably 35 mass % or less, more preferably 25 mass % or less, still more preferably 15 mass % or less. When the amount of the water-soluble components exceeds 35 mass %, its gel strength may be low and its liquid permeability may drop. Further, when the water absorbent resin particles are used in a diaper for a long time, its absorbing properties (CRC and AAP) may drop as time elapses.

[Production Method of Water Absorbing Agent]

A method according to the present invention for producing a water absorbing agent includes the step of mixing the aforementioned water absorbent resin particles, organic acid (or salt thereof), and water-soluble multivalent metal salt.

Note that, the organic acid (or salt thereof) and the water-soluble multivalent metal salt that are contained in the water absorbing agent obtained in the present invention may independently exist or may be contained as a product which has partially reacted, i.e., as organic acid metal salt.

An amount of the water absorbent resin particles serving as a main component of the water absorbing agent is 70 mass % or more and less than 100 mass %, preferably 80 mass % or more and less than 100 mass %, more preferably 90 mass % or more and less than 100 mass %, most preferably 95 mass % or more and less than 100 mass %.

The water-soluble multivalent metal salt is powdery salt of at least bivalent metal. On assumption that a water absorbing agent produced in the present invention is used in an absorbent core for a sanitary material such as a diaper, it is preferable not to color the water absorbing agent and it is preferable to select a water absorbing agent which is harmless for a human body.

In order to efficiently keep an effect of the water-soluble metal salt for a long time at the time of liquid absorption, it is preferable to select water-soluble multivalent metal salt which can be dissolved in pure water at normal temperature so that its concentration is 5 mass % or more, more preferably 10 mass % or more, still more preferably 20 mass % or more.

Examples of the water-soluble multivalent metal salt which can be used in the present invention include: aluminum chloride, polyaluminum chloride, aluminum sulfate, aluminum nitrate, bis aluminum potassium sulfate, bis aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, and zirconium nitrate. Further, it is preferable to use salt containing the crystal water for better solubility with respect to absorbed liquid such as urine. It is particularly preferable to use aluminum compounds. Among them, it is preferable to use aluminum chloride, poly aluminum chloride, aluminum sulfate, aluminum nitrate, bis aluminum potassium sulfate, bis aluminum sodium sulfate, potassium alum, ammonium alum, sodium alum, sodium aluminate. Aluminum sulfate is particularly preferable. It is possible to most favorably use powder of hydrated crystal such as aluminum sulfate octadecahydrate and aluminum sulfate hydrate (tetradecahydrate to octadecahydrate). These components may be independently used or in a suitable combination of two or more kinds.

It is preferable that: the water-soluble multivalent metal salt which can be used in the present invention is particulate, and a particle diameter thereof is smaller than a particle diameter of the water absorbent resin particle in terms of a mixing property. Its mass average particle diameter is preferably 500 μm or less, more preferably 400 μm or less. In terms of performances, more preferably 20 mass % or more, most preferably 30 mass % or more of particles whose particle diameter is 150 μm or less are contained with respect to the whole water-soluble multivalent metal salt.

In the present invention, it is preferable to mix the water-soluble multivalent metal salt, as an aqueous solution, with the water absorbent resin particles. In this case, in order to prevent multivalent metal ion (for example, aluminum ion) from permeating and diffusing in the water absorbent resin particles, the concentration of the aqueous solution is preferably 50 mass % or more, more preferably 60 mass % or more, still more preferably 70 mass % or more, still further more preferably 80 mass % or more, particularly preferably 90 mass % or more, with respect to saturated concentration. Of course, the concentration of the aqueous solution may be the saturated concentration.

The water absorbing agent obtained in the present invention contains preferably 0.001 to 10 parts by mass, more preferably 0.01 to 5 parts by mass, still more preferably 0.1 to 2 parts by mass of the water-soluble multivalent metal salt, with respect to 100 parts by mass of the water absorbent resin particles serving as a main component of the water absorbing agent. It is not preferable that the amount of the water-soluble multivalent metal salt is less than 0.001 parts by mass since it is impossible to improve the desired liquid permeability and anti-blocking property. Further, when the amount of the water-soluble multivalent metal salt exceeds 10 parts by mass, absorbing properties such as CRC and AAP may deteriorate.

Examples of the organic acid (or salt thereof) include: anisic acid, benzoic acid, formate, valeric acid, citric acid, glyoxylic acid, glycolic acid, glutaric acid, succinic acid, tartaric acid, lactic acid, fumaric acid, propionic acid, 3-hydroxy propionic acid, malonic acid, imidino acetic acid, malic acid, isethionic acid, adipic acid, oxalic acid, salicylic acid, gluconic acid, sorbic acid, p-hydroxybenzoic acid, and alkali metal salt such as sodium and potassium thereof; and ammonium salt. Among them, it is preferable to use hydroxy carboxylic acid such as glycolic acid, tartaric acid, lactic acid, 3-hydroxy propionic acid, malic acid, salicylic acid, gluconic acid, and alkali metal salt or ammonium salt thereof. These components may be independently used or in a suitable combination of two or more kinds.

Note that, from examples of the organic acid (or salt thereof), there are excluded acrylic acid and other acrylic-acid-derived reactive by-product, used as material for a water absorbent resin, both of which remain in the water absorbent resin during its polymerization.

By using the organic acid (or salt thereof) in the present invention, it is possible to suppress permeation of the multivalent metal ion (for example, aluminum ion) in the water absorbent resin particles and it is possible to evenly disperse the multivalent metal ion in particle surfaces. Thus, the liquid permeability is greatly improved.

Further, by using the organic acid (or salt thereof) in the present invention, it is possible to solve such a conventional problem that metal components unevenly adhere to a surface of the water absorbent resin in a plane manner. As a result, it is possible to exhibit such an effect that the metal components evenly adhere to an entire vicinity of a surface of the water absorbent resin in a dot manner (the metal components locally exist).

In the present invention, the water absorbent resin particles and the organic acid (or salt thereof) may be mixed without any modification, but it is preferable to mix the water absorbent resin particles, the organic acid (and/or salt thereof), the water-soluble multivalent metal salt, and it is more preferable to mix the water absorbent resin particles, the organic acid (and/or salt thereof) as an aqueous solution, and the water-soluble multivalent metal salt as an aqueous solution, and it is particularly preferable to mix the organic acid (or salt thereof) and the water-soluble multivalent metal salt in the form of common aqueous solution with the water absorbent resin particles. In order to obtain even solution of the water-soluble multivalent metal salt and the organic acid (or salt thereof), it is preferable to use organic acid salt.

The water absorbing agent obtained in the present invention contains preferably 0.1 ppm to 10 parts by mass, more preferably 0.0001 to 5 parts by mass, still more preferably 0.001 to 1 part by mass of the organic acid (or salt thereof), with respect to 100 parts by mass of the water absorbent resin particles serving as a main component of the water absorbing agent. It is not preferable that the amount of the organic acid (or salt thereof) is less than 0.1 ppm since it is impossible to suppress permeation of the metal components into the water absorbent resin and it is impossible to improve the liquid permeability. Further, when the amount of the organic acid (or salt thereof) exceeds 10 parts by mass, absorbing properties such as CRC and AAP may deteriorate.

Further, in the present invention, the organic acid (or salt thereof) and the water-soluble multivalent metal salt may be simultaneously used at the time of surface cross-linking treatment. However, in terms of (i) use of water-soluble multivalent metal salt having causticity with respect to various steel products at high temperature and (ii) easiness in permeation of water-soluble multivalent metal salt into the water absorbent resin particles, it is particularly preferable to mix the water absorbent resin particles whose surfaces have been cross-linked, the organic acid (or salt thereof), and the water-soluble multivalent metal salt.

In the present invention, it is preferable to mix a hydrophilic organic solvent with the water absorbent resin particles in combination with the organic acid (or salt thereof) and the water-soluble multivalent metal salt. It is more preferable that the hydrophilic organic solvent is contained in a common aqueous solution including the organic acid (or salt thereof) and the water-soluble multivalent metal salt.

As the hydrophilic organic solvent, it is possible to use a hydrophilic organic solvent which may be used also in the aforementioned surface cross-linking treatment. Particularly, it is preferable to use polyhydric alcohols such as ethyleneglycol, diethyleneglycol, propyleneglycol, triethyleneglycol, tetraethyleneglycol, polyethyleneglycol, 1,3-propanediol, dipropyleneglycol, 2,2,4-trimethyl-1,3-pentandiol, polypropyleneglycol, glycerin, polyglycerin, 2-butene-1,4-diol, 1,3-butandiol, 1,4-butandiol, 1,5-pentandiol, 1,6-hexanediol, 1,2-cyclohexanedimethanol, 1,2-cyclohexanol, trimethylolpropane, diethanolamine, triethanolamine, polyoxypropylene, oxyethlene-oxypropylene block copolymer, pentaerythritol, and sorbitol. Among them, it is preferable to use ethyleneglycol, propyleneglycol, propanediol, butandiol, pentandiol, hexanediol, glycerin, and trimethylolpropane. These components may be used independently or in a suitable combination of two or more kinds.

The water absorbing agent obtained in the present invention contains preferably more than 0 to 1 part by mass or less, more preferably more than 0 to 0.1 part by mass or less, particularly preferably more than 0 to 0.02 parts by mass or less of the hydrophilic organic solvent with respect to 100 parts by mass of the water absorbent resin particles serving as a main component of the water absorbing agent. By using the hydrophilic organic solvent, it is possible to more evenly mix the water-soluble multivalent metal salt with the water absorbent resin particles.

In the present invention, examples of a device which adds and mixes the organic acid (or salt thereof), the water-soluble multivalent metal salt, and the hydrophilic organic solvent with the water absorbent resin particles whose surfaces have been cross-linked are as follows: a cylindrical mixer, a screw mixer, a screw extruder, a turbulizer, a nauta mixer, a V-shaped mixer, a ribbon blender, a double-arm kneader, a flow mixer, an air current mixer, a rotary disc mixer, a roll mixer, a convolution mixer, and a Lodige mixer. As a mixing method, it is possible to adopt a batch-type mixing method, a sequential mixing method, or a combination thereof. It is more preferable to adopt the sequential mixing method in terms of industrial production. A rotational frequency at the time of mixing operation is not particularly limited, but it is preferable to set the rotational frequency so that the water absorbent resin is not damaged. Specifically, the rotational frequency preferably ranges from 1 to 3000 rpm, more preferably from 2 to 500 rpm, still more preferably from 5 to 300 rpm. It is not preferable to set the rotational frequency to be more than 300 rpm since the water absorbent resin becomes powdery which results in drop of the water absorbing property. Further, when the rotational frequency is less than 1 rpm, the mixing operation is not sufficiently performed, so that it is impossible to obtain the desired liquid permeability and anti-blocking property.

Further, powder temperature of the water absorbent resin particles, not having been mixed with the solution, whose surfaces have been cross-linked, is not particularly limited. However, the powder temperature preferably ranges from room temperature to 100° C., more preferably from 50 to 80° C. When the powder temperature exceeds 100° C., the mixing operation is less efficiently performed, so that it is impossible to obtain the desired liquid permeability and anti-blocking property.

A time taken to mix the water absorbent resin particles subjected to the surface cross-linking treatment in the present invention with solution containing the organic acid (or salt thereof), the water-soluble multivalent metal, and the hydrophilic organic solvent is not particularly limited, but preferably ranges from one second to 20 minutes, more preferably from 10 seconds to 10 minutes, still more preferably from 20 seconds to 5 minutes. When the time taken to perform the mixing operation exceeds 20 minutes, it is impossible to obtain a corresponding effect. In this case, the water absorbent resin may become powdery.

Thus, it is most preferable to set conditions for obtaining the water absorbing agent of the present invention as follows: the powder temperature of the water absorbent resin particles whose surfaces had been cross-linked ranges from 50 to 80° C.; the rotational frequency ranges from 5 to 300 rpm; the time taken to perform the mixing operation ranges from 20 seconds to 5 minutes. The water absorbing agent having been subjected to the mixing operation under the foregoing conditions is superior in treatability and is free from problems such as adhesion and agglomeration. Thus, it is not necessary to perform a drying step for improving the treatability of the water absorbing agent having been subjected to the mixing operation.

[Water Absorbing Agent]

In the water absorbing agent obtained in the present invention, permeation of metal components into the water absorbent resin particles is suppressed, and the metal components evenly adhere to an entire surface of the water absorbent resin in a dot manner, so that the water absorbing agent is superior in a centrifuge retention capacity (CRC) and liquid permeability, and is less susceptible to process damage.

A moisture content of the water absorbing agent obtained by the present invention is preferably less than 10 mass %, particularly preferably less than 5 mass %.

A centrifuge retention capacity (CRC) of the water absorbing agent obtained in the present invention is preferably 10 (g/g) or more, more preferably 20 (g/g) or more, still more preferably 25 (g/g) or more. An upper limit of the centrifuge retention capacity (CRC) is not particularly limited, but is preferably 50 (g/g) or less, more preferably 45 (g/g) or less, still more preferably 40 (g/g) or less. In case where the centrifuge retention capacity (CRC) is less than 10 (g/g), an amount of absorbed liquid is so small that the water absorbing agent is not suitable for use in a sanitary material such as a diaper. Further, in case where the centrifuge retention capacity (CRC) exceeds 50 (g/g), its gel strength is low, so that it may be impossible to obtain a water absorbing agent which is superior in liquid permeability.

An absorbency against pressure (AAP) of the water absorbing agent obtained in the present invention is preferably 18 (g/g) or more, more preferably 20 (g/g) or more, still more preferably 22 (g/g) or more, where the pressure is 4.83 kPa. In case where the absorbency against pressure of 4.83 kPa (AAP) is less than 18 (g/g), when the water absorbing agent is used in a diaper for example, a so-called re-wet amount (an amount of returning liquid which had been absorbed) is large which results in skin rash of a baby.

A saline flow conductivity (SFC) of the water absorbing agent obtained in the present invention is preferably $30 \times 10^{-7}$ $cm^3 \cdot s \cdot g^{-1}$ or more, more preferably $60 \times 10^{-7}$ $cm^3 \cdot s \cdot g^{-1}$ or more, still more preferably $100 \times 10^{-7}$ $cm^3 \cdot s \cdot g^{-1}$ or more. In case where the saline flow conductivity (SFC) is less than $30 \times 10^{-7}$ $cm^3 \cdot s \cdot g^{-1}$, when concentration of the water absorbent resin particles in a core of a diaper is 30 mass % or more (more specifically, when concentration of the water absorbent resin particles in a core of a diaper is 50 mass % or more), a rate at which urine is absorbed is low. This may result in leakage.

It was found that: when the water absorbent resin particles whose surfaces had been cross-linked and the solution containing the organic acid (or salt thereof), the water-soluble multivalent metal salt, and the hydrophilic organic solvent are mixed with each other in order to obtain the water absorbing agent of the present invention, a blocking property between mixture particles significantly drops. As an index for making the drop clearer, an initial blocking ratio shown in each of Examples is used. As this value is lower, the added solution is more evenly diffused over the particles in short time. This also shows that: liquid absorption in local particles is suppressed, and permeation of multivalent metal components into the water absorbent resin is suppressed.

The initial blocking ratio preferably ranges from 0 to 15 mass %, more preferably from 0 to 10 mass %, most preferably from 0 to 5 mass %. When the initial blocking ratio exceeds 15 mass %, the water absorbent resin particles to which the solution has been added are highly likely to adhere and agglomerate, so that treatability of the powder is low. Further, the favorable mixing is not realized, so that it is impossible to improve the liquid permeability and liquid diffusion property despite of a large amount of the multivalent metal components added. Moreover, it is necessary to extend the time taken to perform the mixing operation.

An amount of water-soluble components of the water absorbing agent obtained in the present invention is preferably 35 mass % or less, more preferably 25 mass % or less, still more preferably 15 mass % or less. In case where the amount of the water-soluble components exceeds 35 mass %, its gel strength is low which drops liquid permeability. Further, when the water absorbing agent is used in a diaper, absorbencies (CRC and AAP) may drop as time elapses.

A moisture absorption blocking property of the water absorbing agent of the present invention is represented by a blocking ratio. A specific example of a method for measuring the blocking ratio is as follows: as shown in Examples, the water absorbing agent (or the water absorbent resin particles) is evenly spread on a bottom of a predetermined cup and is made to absorb moisture at 25° C. with relative humidity of 70% or at 25° C. with relative humidity of 80% for one hour, and then is sieved by a shaking classifier for a certain time, so as to measure a moisture absorption blocking ratio in accordance with a mass W4 (g) of the water absorbing agent (or the water absorbent resin particles) remaining on the sieve and a mass W5 (g) of the water absorbing agent (or the water absorbent resin particles) passing through the sieve.

When the moisture absorption blocking ratio is measured in accordance with the foregoing method, the moisture absorption blocking ratio at 25° C. with relative humidity of 70% ranges from 0 to 10 mass %, preferably from 0 to 5 mass %, most preferably from 0 to 3 mass %. The moisture absorption blocking ratio at 25° C. with relative humidity of 80% ranges from 0 to 40 mass %, preferably from 0 to 30 mass %, more preferably from 0 to 20 mass %, most preferably from 0 to 10 mass %. Under any condition, when the moisture absorption blocking ratio exceeds its upper limit, the treatability of the water absorbing agent is low in high humidity. Thus, at the time of production of a thin absorbent core for a sanitary material, there occur the following problems: in a production plant, the water absorbing agent and/or the water absorbent resin particles are coagulated and jammed in a transportation pipe, and it is impossible to evenly mix them with a hydrophilic fiber.

Further, the water absorbing agent obtained in the present invention is characterized in that: the organic acid (or salt thereof) is used to suppress permeation of the multivalent metal components into the particles and to cause the multivalent metal components to locally exist in a vicinity of surfaces of the water absorbent resin particles. A property of the multivalent metal components which locally exist in a vicinity of surfaces of the water absorbent resin particles is represented by a ratio at which the multivalent metal components are extracted in one hour (described in Examples).

As to the extraction of the multivalent metal components in the vicinity of surfaces of the particles, a condition under which it is possible to extract a large amount of multivalent metal components in a short time such as one hour means that: permeation of the multivalent metal components into the water absorbent resin particles is suppressed and the multivalent metal components locally exist in the vicinity of the surfaces.

The permeation of the multivalent metal components into the water absorbent resin is suppressed so as to suppress drop in CRC and AAP and so as to improve the moisture absorption blocking ratio in high humidity, thereby obtaining remarkably superior liquid permeability and liquid diffusion property. In order to realize such advances, a ratio at which the multivalent metal components are extracted in one hour preferably ranges from 5.0 to 100.0 mass %, more preferably from 10.0 to 90.0 mass %, most preferably from 15.0 to 80.0 mass %.

When the ratio at which the multivalent metal components are extracted is less than 5.0 mass %, the multivalent metal components further permeate the water absorbent resin. Thus, the permeation causes CRC and AAP to drop, so that the moisture absorption blocking property is not improved in high humidity despite of a large amount of the multivalent metal components added. Moreover, the liquid permeability and liquid dispersion property are not improved.

[Absorbent Core]

The water absorbing agent obtained in the present invention is combined with a suitable material, thereby obtaining favorable absorbent core serving as an absorbing layer of a sanitary material for example. The following describes the absorbent core.

The absorbent core is a composition, used in sanitary materials such as a disposable diaper; a sanitary napkin, an incontinence pad, a medical pad, to absorb blood, body fluid, and urine. The composition contains the water absorbing agent and other materials. An example of the material used is a cellulose fiber. Specific examples of the cellulose fiber include: wood pulp fibers such as a mechanical pulp, a chemical pulp, a semi-chemical pulp, a dissolved pulp, and the like, that are extracted from wood; artificial cellulose fibers such as rayon and acetate; and the like. Among the cellulose fibers it is preferable to use the wood pulp fiber. Each of these cellulose fibers may partially contain a synthesis fiber such as polyester. In case of using the water absorbing agent obtained in the present invention as a part of the absorbent core, a mass of the water absorbing agent obtained in the present invention is preferably 20 mass % or more. When the mass of the water absorbing agent obtained in the present invention is less than 20 mass %, it may be impossible to obtain a sufficient effect.

In order to obtain the absorbent core by using the water absorbing agent obtained in the present invention and the cellulose fiber, an appropriate method is selected, for example, from the following known methods: a method in which the water absorbing agent is dispersed on paper or a mat made from cellulose fiber and the dispersed water absorbing agent is held by the paper or mat as required; a method in which the cellulose fiber and the water absorbing agent are evenly blended with each other; and a similar method. It is preferable to adopt a method in which the water absorbing agent and the cellulose fiber are dry mixed with each other and then are compressed. According to this method, it is possible to remarkably suppress the water absorbing from falling away from the cellulose fiber. It is preferable to perform the compression while heating, and a temperature range at this time is 50 to 200° C. Further, in order to obtain the absorbent core, a method recited in Japanese Unexamined Patent Publication Tokuhyouhei 9-509591 and a method recited in Japanese Unexamined Patent Publication Tokukaihei 9-290000 are favorably adopted.

The water absorbing agent obtained in the present invention is superior in properties. Thus, when the water absorbing agent is used in the absorbent core, it is possible to obtain an extremely superior absorbent core which quickly absorbs liquid and has little liquid remaining on a surface layer thereof.

The water absorbing agent obtained in the present invention has a superior water absorbing property. Thus, the water absorbing agent can be used as a water absorbing/retaining agent in various use. For example, it is possible to use the water absorbing agent in: absorbing article water absorbing/retaining agents such as a disposable diaper, a sanitary napkin, an incontinence pad, and a medical pad; agriculture/horticulture water retaining agents such as an alternative bog moss, a soil reforming/improving agent, a water retaining agent, and an agrichemical effect maintaining agent; architectural water retaining agents such as an interior wall condensation preventing agent, and a cement additive; a release control agent; a cold insulation agent; a disposable body warmer; a sewage coagulator; a food freshness maintaining agent; an ion exchange column material; a sludge or oil dehydrating agent; a desiccating agent; a humidity controlling agent; and the like. Further, the water absorbing agent obtained in the present invention is favorably used in an absorbing sanitary material, such as a disposable diaper and a sanitary napkin, which absorbs feces, urine, and blood.

In case where the absorbent core is used in sanitary materials such as a disposable diaper, a sanitary napkin, an incontinence pad, a medical pad, it is preferable to arrange the absorbent core so as to include: (a) a liquid permeable top sheet disposed adjacent to a body of the user, (b) a liquid impermeable back sheet disposed adjacent to a clothe of the user so as to be away from the body of the user, and (c) an absorbent core disposed between the top sheet and the back sheet. The absorbent core may be arranged so as to be two-or-more-layered, or may be used with a pulp layer.

EXAMPLES

The following description specifically explains the present invention, but the present invention is not limited to this. Note that, for convenience in description, "part by mass" is referred to merely as "part", and "litter" is referred to merely as "L".

Properties of the water absorbent resin particles or the water absorbing agent were measured in accordance with the following method. Further, when a specific condition is not described, this means that all the operations were performed at room temperature (20 to 25° C.) and at humidity of 50 RH %.

Note that, in case of the water absorbing agent used as a final product such as a sanitary material, the water absorbing agent absorbed moisture, so that the water absorbing agent was separated from the final product as required and properties thereof were measured after being subjected to reduced-pressure low-temperature drying (for example, at 1 mmHg or less and at 60° C. for 12 hours). Further, a moisture content of each of the water absorbing agents used in Examples and Comparative Examples of the present invention was 6 mass % or less.

<Centrifuge Retention Capacity (CRC)>

The centrifuge retention capacity (CRC) represents an absorption capacity at which 0.90 mass % of saline is absorbed for 30 minutes without any pressure. Note that, the CRC is sometimes referred to as an absorbency without load.

0.200 g of water absorbent resin particles or a water absorbing agent was evenly contained in a bag (85 mm×60 mm) made of a nonwoven fabric (Heatron Paper made by Nangoku Pulp Kogyo Co., Ltd.: model type is GSP-22). Then, the bag was heat-sealed. Thereafter, the bag was soaked in an excessively large amount (generally, about 500 ml) of 0.90 mass % physiological saline (sodium chloride aqueous solution) whose temperature had been adjusted to room temperature, and was withdrawn 30 minutes later. By using a centrifugal separator (centrifugal machine made by KOKUSAN Corporation: model type is H-122), the bag was drained for three minutes at a centrifugal force (250 G) recited in edana ABSORBENCY II 441,1-99, and a mass W1 (g) of the bag was measured. Further, the same operation was performed without using the water absorbent resin particles or the water absorbing agent, and a mass W0 (g) was measured. Then, from the masses W1 and W0, a centrifuge retention capacity (CRC) (g/g) was calculated according to the following equation.

Centrifuge retention capacity (g/g)=((mass $W1$ (g)− mass $W0$ (g))/mass (g) of water absorbent resin particles or water absorbent)−1

<Absorbency Against Pressure (AAP)>

The absorbency against pressure (AAP) represents an absorbency at which 0.90 mass % of saline is absorbed for 60 minutes at 4.83 kPa. Note that, the AAP is referred to also as an absorbency against pressure of 4.83 kPa.

By using an apparatus shown in FIG. 1, the absorbency against pressure (AAP) was measured. On a bottom of a plastic supporting cylinder 100 having a 60 mm internal diameter, a metal gauze 101 of stainless-steel 400 mesh (mesh size of 38 μm) was fusion-bonded. Then, under a condition of a room temperature (20° C. to 25° C.) and 50 RH % relative humidity, 0.900 g of water absorbent resin particles or a water absorbing agent was evenly spread on the mesh. Subsequently, a piston 103 and a load 104 were placed in this order on the water absorbent resin particles or the water absorbing agent. External diameters of the piston 103 and the load 104 were slightly smaller than 60 mm which was the internal diameter of the supporting cylinder 100, so that there is no gap between the piston and the supporting cylinder, and upward and downward movements of the piston 103 and the load 104 would not be hampered. Note that, the piston 103 and the load 104 were so adjusted as to evenly apply a 4.83 kPa (0.7 psi) load onto the water absorbent resin particles or the water absorbing agent. Then, a mass Wa (g) of this measurement set was measured.

Inside a petri dish 105 having a 150 mm diameter, a glass filter 106 (product of Sougo Rikagaku Glass Seisakusho Co., Ltd.; diameter of fine pores: 100 μm to 120 μm) having a 90 mm diameter was placed. Thereafter, a 0.90 mass % of sodium chloride solution 108 whose temperature had been adjusted to 20° C. to 25° C. was added until it reached a level of an upper surface of the glass filter 106. Then, a piece of filter paper (product of Advantec Toyo Kaisha, Ltd.; product name: JIS P3801, No. 2; thickness: 0.26 mm; diameter of retained particles: 5 μm) having a 90 mm diameter was placed thereon, so that an entire surface of the filter paper 107 was wetted. An excess of the 0.90 mass % saline 108 was removed.

The measuring apparatus set was placed on the wet filter paper 107. Then, the water absorbent resin particles or the water absorbing agent was made to absorb the 0.90 mass % saline 108 for one hour under the load of 4.83 kPa (0.7 psi). One hour later, the measuring apparatus set having absorbed the 0.90 mass % saline 108 was lifted, and a mass Wb (g) thereof was measured. From the masses Wa and Wb, the absorbency against pressure (AAP) (g/g) was calculated according to the following equation. Absorbency against pressure $$(AAP) = (Wb\ (g) - Wa\ (g))/\text{mass }(0.900)\text{ g of water absorbent resin particles or water absorbing agent}$$

<Saline Flow Conductivity (SFC)>

The saline flow conductivity is a value indicative of liquid permeability when water absorbent resin particles or a water absorbing agent is swollen. The higher the SFC is, the higher the liquid permeability is.

Calculation of the saline flow conductivity was performed in accordance with a saline flow conductivity (SFC) test recited in Published Japanese Translations of International Publication of Patent Application No. 509591/1997 (Tokuhyohei 9-509591).

Figure 2:
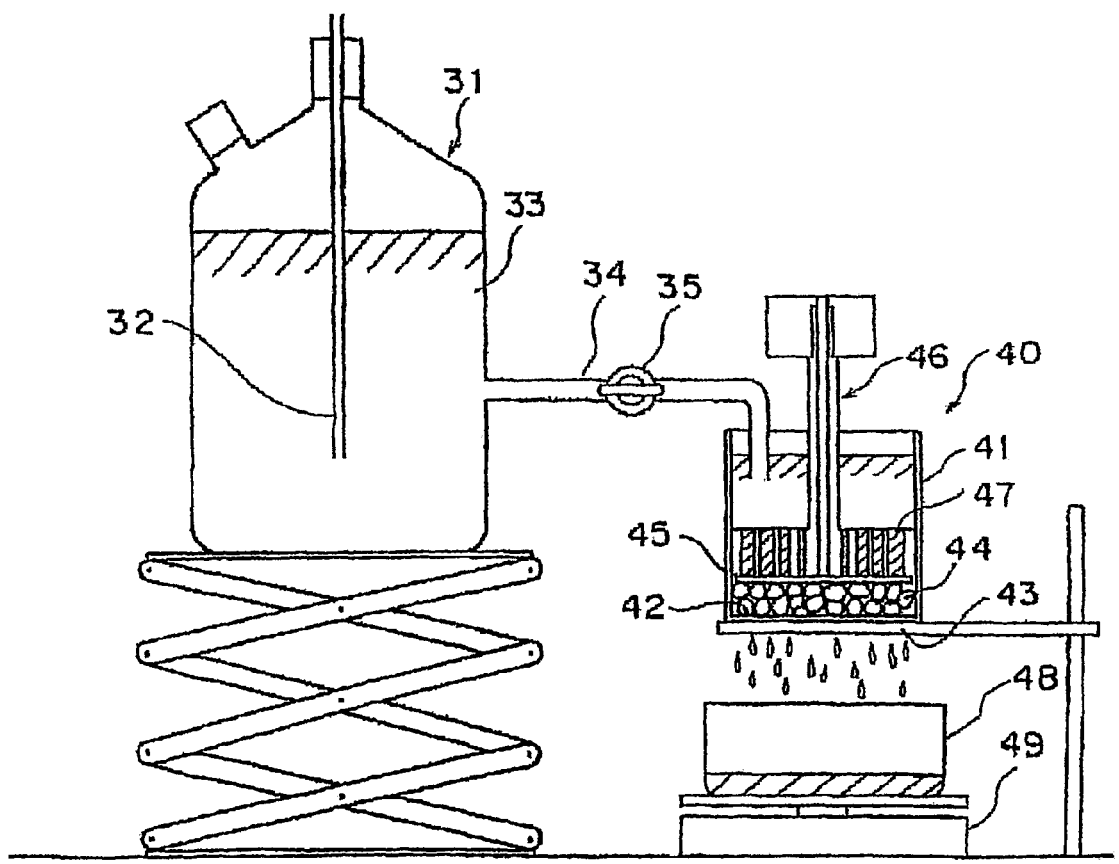
FIG. 2 schematically illustrates an arrangement of an apparatus for measuring SFC which is a value indicative of a performance of the water absorbing agent according to the present invention.

By using an apparatus shown in FIG. 2, the water absorbent resin particles or the water absorbing agent (0.900 g) evenly spread in a container 40 was swollen in a synthesized urine (1) under a pressure of 0.3 psi (2.07 kPa) for 60 minutes, and a height of a gel layer of a gel 44 was recorded. Then, 0.69 mass % sodium chloride solution 33 was made to flow from a tank 31 and to pass through the swollen gel layer at a constant hydrostatic pressure. The SFC test was performed at room temperature (20 to 25° C.). By using a computer and a scale, an amount of liquid passing through the gel layer at intervals of 20 seconds was recorded for 10 minutes as a time function. A flow rate Fs(t) of the solution passing through the swollen gel 44 (mainly between particles thereof) was determined in terms of g/s by dividing an increasing weight (g) by an increasing time (s). A time in which a constant hydrostatic pressure and a stable flow rate had been obtained was set as "Ts", and only data obtained between "Ts" and a ten-minute interval was used to calculate the flow rate, the flow rate calculated between "Ts" and a ten-minute interval was used to calculate a value of Fs (t=0), i.e., a first flow rate of the solution passing through the gel layer. Fs (T=0) was calculated by extrapolating T=0 from a result obtained by approximating a function indicative of a relationship between Fs (T) and T.

$$\text{Saline flow conductivity } (SFC) = (Fs(t=0) \times L0)/(\rho \times A \times \Delta P)$$
$$= (Fs(t=0) \times L0)/139506$$

Here,

Fs (t=0): a flow rate represented by "g/s"
L0: a height of the gel layer that is represented by "cm"
ρ: a density (1.003 g/cm³) of NaCl solution
A: an area (28.27 cm²) on the upper side of the gel layer of the cell 41

ΔP: a hydrostatic pressure (4920 dyne/cm²) exerted to the gel layer. Further, a unit of the saline flow conductivity (SFC) is $(10^{-7} \times \text{cm}^3 \times s \times g^{-1})$.

In the apparatus shown in FIG. 2, a glass tube 32 was inserted into the tank 31, and a lower end of the glass tube 32 was disposed so that 0.69 mass % sodium chloride solution 33 was positioned 5 cm higher than a bottom of the swelling gel 44 in the cell 41. 0.69 mass % sodium chloride solution 33 contained in the tank 31 was supplied to the cell 41 via an L-shaped tube 34 with a cock. A collecting container 48 for collecting liquid having passed through the gel layer was disposed under the cell 41, and the collecting container 48 was placed on an even balance 49. An inside diameter of the cell 41 was 6 cm, and No. 400 stainless metal gauze (38 μm in mesh) 42 was placed on a bottom of a lower portion of the cell 41. A hole 47 which allowed liquid to pass through was provided on a lower portion of a piston 46, and a glass filter 45 having high permeability was provided on the bottom thereof so that (i) the water absorbent resin particles or the water absorbing agent or (ii) the swelling gel did not enter into the hole 47. The cell 41 was placed on a table for the cell, and the table's surface which is in contact with the cell was positioned on the stainless metal gauze 43 which did not prevent the liquid from passing through.

The synthesized urine (1) was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of pure water.

<Mass Average Particle Diameter (D50) and Logarithmic Standard Deviation (δξ) of Particle Size Distribution>

The water absorbent resin particles or the water absorbing agent was sieved by using JIS standard sieves respectively having mesh sizes of 850 μm, 710 μm, 600 μm, 500 μm, 425 μm, 300 μm, 212 μm, 150 μm, 45 μm, and the like, and a residual percentage R was plotted on a logarithmic probability paper. Then, a particle diameter corresponding to R=50 mass % was read as the mass average particle diameter (D50). Further, assuming that X1 is a particle diameter in case where R=84.1% and X2 is a particle diameter in case where R=15.9%, the logarithmic standard deviation (δξ) is represented by the following equation. As a value of δξ is smaller, the particle size distribution is narrower.

$$\delta\xi = 0.5 \times \ln(X2/X1)$$

Classification in measuring the logarithmic standard deviation (δξ) of the particle size distribution was performed as follows: 10.0 g of the water absorbent resin particles or the water absorbing agent was spread on JIS standard sieves (THE IIDA TESTING SIEVE: diameter is 8 cm) respectively having mesh sizes of 850 μm, 710 μm, 600 μm, 500 μm, 425 μm, 300 μm, 212 μm, 150 μm, and 45 μm, and was classified by using a sieve shaker (IIDA SIEVE SHAKER, TYPE: ES-65 (rotational frequency: 60 Hz 230 rpm, impact: 60 Hz 130 rpm), SER. No. 0501) for five minutes at the room temperature (20° C. to 25° C.) under the humidity of 50 RH %.

<Blocking Ratio (BR)>

The blocking ratio is a value obtained at 25° C., at 70 RH %, in an hour.

2.00 g of water absorbent resin particles or a water absorbing agent was evenly spread on a bottom of a predetermined cup whose inside diameter was 50 mm and height was 10 mm, and was quickly placed in a constant-temperature-and-moisture apparatus (PLATINOUS LUCIFFER PL-2G, product of TABAI ESPEC CORPORATION) in which temperature had been adjusted to 25° C. and relative humidity had been adjusted to 70%. Then, the water absorbent resin particles or the water absorbing agent was left in the constant-temperature-and-moisture apparatus for 60 minutes. Thereafter, the water absorbent resin particles or the water absorbing agent that had absorbed moisture was moved onto a JIS standard sieve (diameter is 7.5 cm, mesh size is 2000 μm), and was sieved for five minutes by using a sieve shaker (IIDA SIEVE SHAKER, TYPE: ES-65 (rotational frequency: 60 Hz 230 rpm, impact: 60 Hz 130 rpm), SER. No. 0501). Then, a mass W4 (g) of the water absorbent resin particles or the water absorbing agent which remained on the sieve and a mass W5 (g) of the water absorbent resin particles or the water absorbing agent which had passed through the sieve were measured.

Then, the blocking ratio (mass %) was calculated in accordance with the following equation. As the moisture absorption blocking ratio is lower, the water absorbent resin particles or the water absorbing agent is superior in terms of the fluidity at the time of moisture absorption.

$$\text{Blocking ratio(BR)(mass \%)} = \text{mass } W4 \text{ (g)}/(\text{mass } W4 \text{ (g)} + \text{mass } W5 \text{ (g)}) \times 100$$

Note that, the constant-temperature-and-moisture apparatus was set under stricter conditions of 25° C. and 80 RH %, and the same operation as the foregoing-operation was performed, thereby measuring a blocking ratio.

<Initial Blocking Ratio (IBR)>

The initial blocking ratio is a blocking ratio right after various kinds of additive are mixed with the water absorbent resin particles under conditions of 25° C. and 50 RH ° A).

30 g of the water absorbent resin particles whose surfaces had been cross-linked by performing a heating treatment or using an organic cross-linking agent was mixed with water-soluble multivalent metal salt and/or organic acid (or salt thereof) and/or hydrophilic organic solvent (amounts thereof are specified in Examples). In 30 seconds after beginning of the mixing operation, 10.0 g of thus obtained mixture was quickly moved onto a JIS standard sieve having a diameter of 7.5 cm and mesh of 850 μm. Right after the JIS standard sieve was closed with its lid (within one minute from beginning of the mixing operation), the sieve was shaken by a sieve shaker. (IIDA SIEVE SHAKER, TYPE: ES-65 (rotational frequency: 60 Hz 230 rpm, impact: 60 Hz 130 rpm), SER. No. 0501) for five minutes, a mass W6 (g) of a water absorbing agent remaining on the sieve and a mass W7 (g) of a water absorbing agent passing through the sieve were measured. Then, the initial blocking ratio (mass %) was calculated in accordance with the following equation.

$$\text{Initial blocking ratio(mass \%)} = \text{mass } W6 \text{ (g)}/(\text{mass } W6 \text{ (g)} + \text{mass } W7 \text{ (g)}) \times 100$$

As the initial blocking ratio is lower, the additive is more evenly mixed with the whole water absorbent resin particles in a short time. This also shows that formation of any agglomeration is suppressed.

<Quantity of Water-Soluble Component (Extractable Polymer Content)>

184.3 g of a 0.90 mass % saline was measured and poured into a 250 ml plastic container having a cover. Into the saline, 1.00 g of water absorbent resin particles or a water absorbing agent was added, and the saline was stirred for 16 hours by rotating a stirrer, thereby preparing a water-soluble component extract solution. The water-soluble component extract solution was filtered through a piece of filter paper (product of Advantec Toyo Kaisha, Ltd.; product name: JIS P3801, No. 2; thickness: 0.26 mm; diameter of retained particles: 5 μm), thereby obtaining a filtrate. 50.0 g of the filtrate was measured, and used as a measurement solution.

First, 0.90 mass % of the saline to which the water absorbent resin particles or the water absorbing agent had not been added was titrated by using a 0.1 N NaOH solution, until pH of the saline reached 10. In this way, a titration amount ([bNaOH] ml) of 0.1N NaOH solution which was required so that pH of the saline reached 10 was measured. After that, the 0.1N HCl solution was titrated until pH of the saline reached 2.7. In this way, a titration amount ([bHCl] ml) of 0.1N HCl solution which was required so that pH of the saline reached 2.7 was measured.

The same titration was performed with respect to the measurement solution. As a result, a titration amount ([NaOH] ml) of 0.1N NaOH solution which was required so that pH of the measurement solution reached 10 was measured, and a titration amount ([HCl] ml) of 0.1N HCl solution which was required so that pH of the measurement solution reached 2.7 was obtained.

For example, in case where a water absorbent resin composition includes a known amount of acrylic acid and its sodium chloride, it is possible to calculate a quantity of soluble component in the water absorbent resin particles or the water absorbing agent in accordance with the following equation. In case of an unknown quantity, an average molecular weight of the monomer is calculated in accordance with a neutralization ratio obtained by the titration.

$$\text{Quantity of soluble component (mass \%)} = 0.1 \times (\text{average molecular weight}) \times 184.3 \times 100 \times ([\text{HCl}] - [b\text{HCl}])/1000/1.0/50.0$$

$$\text{Neutralization ratio(mol \%)} = (11[\text{NaOH}] - [b\text{NaOH}])/([\text{HCl}] - [b\text{HCl}])) \times 100$$

<Extraction Rate of Multivalent Metal (ERM)>

(Method for Determining a Quantity of Multivalent Metal Contained in the Water Absorbing Agent)

1.0 g of the water absorbing agent was measured and placed in a polypropylene beaker of 260 ml, and 190.0 g of physiological saline (0.9 mass % NaCl aqueous solution) and 10.0 g of 2N hydrochloric acid were added thereto, and thus obtained mixture was stirred for 30 minutes at room temperature. After stirring them, supernatant liquid thereof was filtered by using a chromatdisc (GL Chromatdisc 25A, product of GL Science Inc.), and was analyzed by plasma emission spectrochemical analysis (by using ULTIMA, product of HORIBA, Ltd.), thereby calculating the multivalent metal component concentration. Note that, an analytical curve was made in accordance with physiological saline containing a known amount of the multivalent metal component. On the basis of the calculated multivalent metal component concentration, the multivalent metal component concentration in the water absorbing agent is represented by the following equation.

$$\text{Multivalent metal component concentration(mass \%)} \\ \text{in the water absorbing agent} = (\text{multivalent metal component concentration (mass \%) in solution}) \times 200$$

(Method for Measuring Multivalent Metal Component Extraction Rate)

Solution A was prepared by mixing 95 g of methanol solution of 1.0 mass % 8-quinolinol (product of Wako Pure Chemical Industries, Ltd.) with 5 g of pure water, and solution B was prepared by mixing 95 g of methanol with 5 g of pure water.

A teflon (registered trademark) rotor whose diameter was 35 mm was placed in a 260 ml polypropylene container, and 5 g of the water absorbing agent and 25 g of the solution A were measured and poured therein. The container was tightly closed, and the content was stirred by using a magnetic stirrer for one hour at room temperature. 5 ml of supernatant liquid thereof was picked up by using a polypropylene syringe, and a chromatdisc (GL chromatdisc 25A, product of GL Science Inc.) was provided on the syringe, and the filtered liquid was placed in a polypropylene container. Part of the filtered liquid was moved to a 1 cm cell made of plastic, and a light absorbance at which a complex constituted of the multivalent metal component and 8-quinolinol absorbs light of specific wavelength was measured by using a spectrophotometer (Hitachi ratio beam spectrophotometer U-1100). For example, when the multivalent metal component is aluminum, the specific wavelength was 380 nm. Hereinafter, for the convenience in description, the specific wavelength is explained on the assumption that the multivalent metal component is aluminum. When the light absorbance at which the filtered liquid absorbed light having 380 nm wavelength exceeded a measurement limit of the spectrophotometer, the filtered liquid was diluted by the solution B so that the light absorbance was within a measurable range of the spectrophotometer. Then, the measurement was performed.

Further, as the light absorbance at the time of extraction of 100 mass % multivalent metal component, measurement was performed with respect also to a light absorbance at which light of 380 nm wavelength was absorbed by a solution obtained by dissolving the multivalent metal component in the solution A so that there is the same amount of the multivalent metal component as at the time of extraction of 100 mass % multivalent metal component (the concentration of the multivalent metal component in the water absorbing agent was separately measured in the foregoing manner).

The extraction rate of the multivalent metal component was calculated in accordance with the following equation.

Extraction rate(mass %) of the multivalent metal component=((filtered liquid's light absorbance with respect to light of 380 nm wavelength)–(solution $A$'s light absorbance with respect to light of 380 nm wavelength))/(light absorbance with respect to light of 380 nm wavelength at the time of extraction of 100 mass % multivalent metal component)×100

<Paint Shaker Test>

The paint shaker test (PS) was performed as follows. 10 g of glass beads whose diameter was 6 mm and 30 g of water absorbent resin particles or a water absorbing agent were placed in a glass container whose diameter was 6 cm and height was 11 cm. Then, the glass container was provided on a paint shaker (product of Toyo Seiki Seisaku-syo, LTD: product No. 488), and was shaken at 800 cycle/min (CPM). An apparatus used in this test is detailed in Japanese Unexamined Patent Publication No. 235378/1997 (Tokukaihei 9-235378).

A test in which a time taken to shake the glass container was 30 minutes was a paint shaker test 1. A test in which a time taken to shake the glass container was 10 minutes was a paint shaker test 2.

After shaking the glass container, the glass beads were removed by using a JIS standard sieve (2 mm in mesh), thereby obtaining water absorbent resin particles or a water absorbing agent which had been damaged.

Production Example 1

505.6 g of acrylic acid; 4430.8 g of 37 mass % sodium acrylate aqueous solution, 497.0 g of pure water, and 12.79 g of polyethyleneglycoldiacrylate (molecular weight was 523) were dissolved in a reactor that had been prepared by placing a lid on a 10 L stainless-steel double-arm kneader equipped with two sigma blades and a jacket, thereby obtaining a reaction solution. Then, the reaction solution was deaerated for 20 minutes in an atmosphere of nitrogen gas. Subsequently, 29.34 g of 10 mass % sodium persulfate and 24.45 g of 0.1 mass % L-ascorbic acid aqueous solution were added to the reaction solution, while the reaction solution was stirred. Approximately one minute later, polymerization was initiated. During the polymerization, the reaction solution was kept at 20° C. to 95° C. while the generated gel was being pulverized. After 30 minutes from the initiation of the polymerization, the cross-linked hydrogel polymer was removed from the reactor. Thus obtained cross-linked hydrogel polymer had been fragmented so that its diameter was approximately 5 mm.

The cross-linked hydrogel polymer fragmented was spread out on a wire mesh of 50 mesh, and was dried by hot air at 180° C. for 50 minutes. A dry polymer thus obtained was pulverized by using a roll mill, and then classified by using a JIS standard sieve whose mesh size was 600 µm and a JIS standard sieve whose mesh size was 150 µm, thereby obtaining a water absorbent resin (1) having an irregularly-pulverized shape. In the water absorbent resin (1), a centrifuge retention capacity was 33.0 g/g and water soluble component was 9.0 mass %.

In 100 parts of thus obtained water absorbent resin (1), a surface cross-linking agent including 0.4 parts by mass of 1,4-butanediol, 0.6 parts by mass of propyleneglycol, and 3.0 parts by mass of pure water, was mixed. The mixture was then heated at 200° C. for 30 minutes. Further, particles thereof were disintegrated so as to pass through a JIS standard sieve whose mesh size was 600 µm. Subsequently, the particles were subjected to the paint shaker test 1, thereby obtaining water absorbent resin particles (A) whose surfaces had been cross-linked.

Table 1 shows properties of the water absorbent resin particles (A).

Example 1

0.02 parts by mass of 90% lactic acid (product of Musashino Chemical Laboratory, Ltd.) was mixed with 2 parts by mass of liquid aluminum sulfate 27 mass % solution for city water (product of ASADA KAGAKU KOGYO KABUSHIKIKAISHA), thereby obtaining transparent and even solution.

2.02 parts by mass of the aqueous solution was evenly mixed with 100 parts by mass of the water absorbent resin particles (A), and was dried at 60° C. for one hour. The dried product was disintegrated so as to pass through a JIS standard sieve (600 µm in mesh). Subsequently, the particles are subjected to the paint shaker test 2, thereby obtaining a water absorbing agent (1).

Table 1 shows properties of the water absorbing agent (1).

Example 2

The same operation was performed as Example 1 except that an amount of the 90% lactic acid was changed to 0.06 parts by mass. A solution (2.06 parts by mass) obtained by mixing the liquid aluminum sulfate 27 mass % solution for city water with the 90% lactic acid was colored slightly milky. In this manner, a water absorbing agent (2) was obtained.

Table 1 shows properties of the water absorbing agent (2).

Example 3

The same operation was performed as Example 1 except that an amount of the 90% lactic acid was changed to 0.2 parts by mass. In a solution (2.2 parts by mass) obtained by mixing the liquid aluminum sulfate 27 mass % solution for city water with the 90% lactic acid, white crystal was deposited. In this manner, a water absorbing agent (3) was obtained.

Table 1 shows properties of the water absorbing agent (3).

Example 4

The same operation was performed as Example 1 except that an amount of the 90% lactic acid was changed to 0.6 parts by mass. In a solution (2.6 parts by mass) obtained by mixing the liquid aluminum sulfate 27 mass % solution for city water with the 90% lactic acid, white crystal was deposited. In this manner, a water absorbing agent (4) was obtained.

Table 1 shows properties of the water absorbing agent (4).

Example 5

The same operation was performed as Example 1 except that 0.02 parts by mass of 50% sodium lactate (product of Musashino Chemical Laboratory, Ltd.) was used instead of the 90% lactic acid. A solution (2.02 parts by mass) obtained by mixing the liquid aluminum sulfate 27 mass % solution for city water with the 50% sodium lactate was a transparent and even solution. In this manner, a water absorbing agent (5) was obtained.

Table 1 shows properties of the water absorbing agent (5).

Example 6

The same operation was performed as Example 5 except that an amount of the 50% sodium lactate was changed to 0.4 parts by mass. A solution (2.4 parts by mass) obtained by mixing the liquid aluminum sulfate 27 mass % solution for city water with the 50% sodium lactate was a transparent and even solution. In this manner, a water absorbing agent (6) was obtained.

Table 1 shows properties of the water absorbing agent (6).

Example 7

The same operation was performed as Example 5 except that an amount of the 50% sodium lactate was changed to 1 part by mass. A solution (3 parts by mass) obtained by mixing the liquid aluminum sulfate 27 mass % solution for city water with the 50% sodium lactate was a transparent and even solution. In this manner, a water absorbing agent (7) was obtained.

Table 1 shows properties of the water absorbing agent (7).

Example 8

The same operation was performed as Example 5 except that an amount of the 50% sodium lactate was changed to 0.2 parts by mass and an amount of the liquid aluminum sulfate 27 mass % solution for city water was changed to 1 part by mass. A solution (1.2 parts by mass) obtained by mixing the liquid aluminum sulfate 27 mass % solution for city water with the 50% sodium lactate was a transparent and even solution. In this manner, a water absorbing agent (8) was obtained.

Table 1 shows properties of the water absorbing agent (8).

Example 9

The same operation was performed as Example 5 except that an amount of the 50% sodium lactate was changed to 0.6 parts by mass and an amount of the liquid aluminum sulfate 27 mass % solution for city water was changed to 3 parts by mass. A solution (3.6 parts by mass) obtained by mixing the liquid aluminum sulfate 27 mass % solution for city water with the 50% sodium lactate was a transparent and even solution. In this manner, a water absorbing agent (9) was obtained.

Table 1 shows properties of the water absorbing agent (9).

Example 10

The same operation was performed as Example 1 except that 0.2 parts by mass of sodium gluconate (product of Wako Pure Chemical Industries, Ltd.) was used instead of the 90% lactic acid. A solution (2.2 parts by mass) obtained by mixing the liquid aluminum sulfate 27 mass % solution for city water with the sodium gluconate was a transparent and even solution. In this manner, a water absorbing agent (10) was obtained.

Table 1 shows properties of the water absorbing agent (10).

Example 11

The same operation was performed as Example 1 except that 0.2 parts by mass of sodium citrate (product of Wako Pure Chemical Industries, Ltd.) was used instead of the 90% lactic acid. A solution (2.2 parts by mass) obtained by mixing the liquid aluminum sulfate 27 mass % solution for city water with the sodium citrate was a transparent and even solution. In this manner, a water absorbing agent (11) was obtained.

Table 1 shows properties of the water absorbing agent (11).

Example 12

The same operation was performed as Example 1 except that 0.2 parts by mass of sodium succinate (product of Wako Pure Chemical Industries, Ltd.) was used instead of the 90% lactic acid. A solution (2.2 parts by mass) obtained by mixing the liquid aluminum sulfate 27 mass % solution for city water with the sodium succinate was a transparent and even solution. In this manner, a water absorbing agent (12) was obtained.

Table 1 shows properties of the water absorbing agent (12).

Example 13

The same operation was performed as Example 1 except that 3 parts by mass of potassium alum aqueous solution (product of TAIMEI CHEMICALS CO., LTD.) was used instead of the liquid aluminum sulfate 27 mass % solution for city water and 0.6 parts by mass of 50% sodium lactate aqueous solution (product of Musashino Chemical Laboratory, Ltd.) was used instead of the 90% lactic acid. A solution (3.6 parts by mass) obtained by mixing the potassium alum aqueous solution with the 50% sodium lactate aqueous solution was a transparent and even solution. In this manner, a water absorbing agent (13) was obtained.

Table 1 shows properties of the water absorbing agent (13).

Example 14

The same operation was performed as Example 1 except that 0.2 parts by mass of 50% sodium lactate aqueous solution (product of Musashino Chemical Laboratory, Ltd.) was used instead of the 90% lactic acid and 0.2 parts by mass of propyleneglycol was additionally used. A solution (2.4 parts by mass) obtained by mixing the liquid aluminum sulfate 27 mass % solution for city water, the 50% sodium lactate aqueous solution, and the propyleneglycol with each other, was a transparent and even solution. In this manner, a water absorbing agent (14) was obtained.

Table 1 shows properties of the water absorbing agent (14).

Production Example 2

A solution (A) was prepared by mixing 185.4 g of acrylic acid, 0.942 g (0.07 mol % with respect to the acrylic acid) of polyethyleneglycoldiacrylate (molecular weight was 523), and 1.13 g of 1.0 mass % diethylenetriamine penta acetic acid penta sodium salt aqueous solution with each other. Further, a solution (B) was prepared by mixing 148.53 g of 48.5 mass % sodium hydroxide aqueous solution with 159.71 g of ion exchange water whose temperature had been adjusted to 50° C. In a polypropylene container, surrounded by polystyrene foam serving as a heat insulator, which had an internal diameter of 80 mm and a capacity of 1 litter, the solution (A) and the solution (B) were quickly mixed with each other in an open manner while being stirred by a magnetic stirrer, thereby obtaining a monomer aqueous solution whose temperature had risen to approximately 100° C. due to heat of neutralization and heat of dissolution.

4.29 g of 3 mass % potassium persulfate was added to thus obtained monomer aqueous solution, and the mixture was stirred for several seconds. Thereafter, the resultant was poured into a stainless tray-type container whose surface was heated up to 100° C. by a hot plate (NEO HOTPLATE H1-100: product of IUCHI SEIEIDO CO., LTD.). The stainless tray-type container was internally coated with teflon (registered trademark), and its bottom size was 250×250 mm and top size was 640×640 mm and height was 50 mm so that its central cross-sectional surface was trapezoid with its top open.

Polymerization was initiated right after the monomer aqueous solution had been poured. The polymerization was promoted while generating vapors and expanding/foaming vertically and horizontally. Thereafter, the resultant dwindled so as to be slightly larger than the bottom size. The expanding/dwindling came to an end within approximately one minute. After the resultant had been left in the container for 4 minutes, a water-containing polymer was removed.

Thus obtained water-containing polymer was pulverized by a meat chopper (ROYAL MEAT CHOPPER VR400K: product of IIZUKA KOGYO KABUSHIKIKAISHA) whose dice diameter was 9.5 mm, thereby obtaining a water-containing polymer that had been fragmented.

The cross-linked hydrogel polymer that had been fragmented was spread out on a wire mesh of 50 mesh, and was dried by hot air at 180° C. for 50 minutes. A dry polymer thus obtained was pulverized by using a roll mill, and then classified by using a JIS standard sieve whose mesh size was 850 μm and a JIS standard sieve whose mesh size was 150 μm, thereby obtaining a water absorbent resin (2), having an irregularly pulverized shape, whose mass average particle diameter was 450 μm. In the water absorbent resin (2), a centrifuge retention capacity (CRC) was 36.0 g/g and a water-soluble component was 12.0 mass %.

In 100 parts of thus obtained water absorbent resin (2), a surface cross-linking agent including 0.4 parts by mass of 1,4-butanediol, 0.6 parts by mass of propyleneglycol, and 3.0 parts by mass of pure water, was evenly mixed. The mixture was then heated at 200° C. for 30 minutes. Further, particles thereof were disintegrated so as to pass through a JIS standard sieve (850 μm in mesh). Subsequently, the particles were subjected to the paint shaker test 1, thereby obtaining water absorbent resin particles (B) whose surfaces had been cross-linked.

Table 1 shows properties of the water absorbent resin particles (B).

Further, in 100 parts of thus obtained water absorbent resin (2), a surface cross-linking solvent including 0.4 parts by mass of 1,4-butanediol, 0.6 parts by mass of propyleneglycol, and 3.0 parts by mass of pure water, was evenly mixed. The mixture was then heated at 200° C. for 40 minutes. Further, particles thereof were disintegrated so as to pass through a JIS standard sieve (850 μm in mesh). Subsequently, the particles were subjected to the paint shaker test 1, thereby obtaining water absorbent resin particles (C) whose surfaces had been cross-linked.

Table 1 shows properties of the water absorbent resin particles (C).

Example 19

The same operation was performed as Example 6 except that the water absorbent resin particles (B) were used, thereby obtaining a water absorbing agent (19).

Table 1 shows properties of the water absorbing agent (19).

Example 20

The same operation was performed as Example 6 except that the water absorbent resin particles (C) were used, thereby obtaining a water absorbing agent (20).

Table 1 shows properties of the water absorbing agent (20).

Comparative Example 1

The same operation was performed as Example 1 except that 0.02 parts by mass of the 90% lactic acid (product of Musashino Chemical Laboratory, Ltd.) was not mixed with 2 parts by mass of the liquid aluminum sulfate 27 mass % solution for city water (product of ASADA KAGAKU KOGYO KABUSHIKIKAISHA) and 2 parts by mass of the liquid aluminum sulfate 27 mass % solution for city water (product of ASADA KAGAKU KOGYO KABUSHIKIKAISHA) was independently used, thereby obtaining a comparative water absorbing agent (1).

Table 1 shows properties of the comparative water absorbing agent (1).

Comparative Example 2

The same operation was performed as Example 19 except that 0.02 parts by mass of the 50% sodium lactate (product of Musashino Chemical Laboratory, Ltd.) was not mixed with 2 parts by mass of the liquid aluminum sulfate 27 mass % solution for city water (product of ASADA KAGAKU KOGYO KABUSHIKIKAISHA) and 2 parts by mass of the liquid aluminum sulfate 27 mass % solution for city water (product of ASADA KAGAKU. KOGYO KABUSHIKIKAISHA) was independently used, thereby obtaining a comparative water absorbing agent (2).

Table 1 shows properties of the comparative water absorbing agent (2).

Comparative Example 3

The same operation was performed as Example 20 except that 0.02 parts by mass of the 50% sodium lactate (product of Musashino Chemical Laboratory, Ltd.) was not mixed with 2 parts by mass of the liquid aluminum sulfate 27 mass % solution for city water (product of ASADA KAGAKU KOGYO KABUSHIKIKAISHA) and 2 parts by mass of the liquid aluminum sulfate 27 mass % solution for city water (product of ASADA KAGAKU KOGYO KABUSHIKIKAISHA) was independently used, thereby obtaining a comparative water absorbing agent (3).

Table 1 shows properties of the comparative water absorbing agent (3).

Example 21

0.4 parts by mass of 50% sodium lactate (product of Musashino Chemical Laboratory, Ltd.) was mixed with 2 parts by mass of liquid aluminum sulfate 27 mass % solution for city water (product of ASADA KAGAKU KOGYO KABUSHIKIKAISHA), thereby obtaining transparent and even aqueous solution.

2.4 parts by mass of the aqueous solution was evenly mixed with 100 parts by mass of the water absorbent resin (1), obtained in Production Example 1, which had an irregularly-pulverized shape, and was dried at 60° C. for one hour. The dried product was sieved by a JIS standard sieve (850 µm in mesh), so that all the particles passed through the sieve. In this manner, a water absorbing agent (21) was obtained.

Table 1 shows properties of the water absorbing agent (21).

Note that, when the 50% sodium lactate was not used, an aggregate was left on a JIS standard sieve, whose mesh size was 850 µm, after being left at 60° C. for one hour and being sieved by the JIS standard sieve.

Comparative Example 4

In 100 parts of the water absorbent resin (1), obtained in Production Example 1, which had an irregularly-pulverized shape, a surface cross-linking agent including 0.4 parts by mass of 1,4-butanediol, 0.6 parts by mass of propyleneglycol, 0.1 parts by mass of 90% lactic acid (product of Musashino Chemical Laboratory, Ltd.), and 3.0 parts by mass of pure water, was evenly mixed. The mixture was then heated at 200° C. for 30 minutes. Further, particles thereof were disintegrated so as to pass through a JIS standard sieve whose mesh size was 600 µm. Subsequently, the particles were subjected to the paint shaker test 1, thereby obtaining a comparative water absorbing agent (4).

Table 1 shows properties of the comparative water absorbing agent (4).

Example 22

There was prepared an even mixture solution including 1 part by mass of liquid aluminum sulfate 27 mass % solution for city water (product of ASADA KAGAKU KOGYO KABUSHIKIKAISHA), 0.2 parts by mass of 50% sodium lactate aqueous solution (product of Musashino Chemical Laboratory, Ltd.), and 0.1 part by mass of propyleneglycol.

Next, a biaxial channel stirrer was used as an apparatus for mixing the foregoing solution by using the water absorbent resin particles (B). A fixed-quantity feeder was used as a mixing apparatus whose jacket temperature had been set to 60° C. and rotational frequency was set to 15 rpm. By using the fixed-quantity feeder, the water absorbent resin particles (B) heated to 60° C. were sequentially supplied at 4 kg/hr, and the foregoing solution was added at 52 g/hr by using a binary spray. The water absorbent resin was mixed in the apparatus for 5 minutes and was discharged. Right after being discharged, the water absorbent resin was disintegrated so as to pass through a JIS standard sieve whose mesh size was 850 µm. Thus obtained water absorbent resin particles were free from any adhesiveness and were extremely powdery. Next, the particles were subjected to the paint shaker test 2. In this manner, a water absorbing agent (22) was obtained.

Table 1 shows properties of the water absorbing agent (22).

Example 23

There was, prepared an even mixture solution including 0.5 parts by mass of liquid aluminum sulfate 27 mass % solution for city water (product of ASADA KAGAKU KOGYO KABUSHIKIKAISHA), 0.1 part by mass of 50% sodium lactate aqueous solution (product of Musashino Chemical Laboratory, Ltd.), and 0.05 parts by mass of propyleneglycol.

Next, a Lödige mixer was used as an apparatus for mixing the foregoing solution by using the water absorbent resin particles (B). 500 g of the water absorbent resin particles (B) whose temperature had been set to 70° C. in advance was placed in a mixing apparatus whose jacket temperature had been set to 70° C., and 3.35 g of the foregoing solution was added by using a pressure spray at a rotational frequency of 250 rpm. The water absorbent resin was mixed in the apparatus for 30 seconds and was discharged. Then, the discharged water absorbent resin was left at room temperature for 3 minutes. Thereafter, the water absorbent resin was disintegrated so as to pass through a JIS standard sieve whose mesh size was 850 µm. Thus obtained water absorbent resin particles were free from any adhesiveness and were extremely powdery. Next, the particles were subjected to the paint shaker test 2. In this manner, a water absorbing agent (23) was obtained.

Table 1 shows properties of the water absorbing agent (23).

Example 24

The same operation was performed as Example 23 except that the water absorbent resin particles (C) were used. In this manner, a water absorbing agent (24) was obtained.

Table 1 shows properties of the water absorbing agent (24).

Production Example 3

436.4 g of acrylic acid, 4617.9 g of 37 mass % sodium acrylate aqueous solution, 381.0 g of pure water, and 11.4 g of polyethyleneglycoldiacrylate (molecular weight was 523) were dissolved in a reactor that had been prepared by placing a lid on a 10 L stainless-steel double-arm kneader equipped with two sigma blades and a jacket, thereby obtaining a reaction solution. Then, the reaction solution was deaerated for 20 minutes in an atmosphere of nitrogen gas. Subsequently, 29.07 g of 10 mass % sodium persulfate and 24.22 g of 0.1 mass % L-ascorbic acid aqueous solution were added to the reaction solution, while the reaction solution was stirred, and polymerization was performed at 20 to 95° C. After 30 minutes from the initiation of the polymerization, the cross-linked hydrogel polymer was removed from the reactor. Thus obtained cross-linked hydrogel polymer had been fragmented so that its diameter was approximately 5 mm.

The cross-linked hydrogel polymer fragmented was spread out on a wire mesh of 50 mesh, and was dried by hot air at 180° C. for 50 minutes. A dry polymer thus obtained was pulverized by using a roll mill, and then classified by using a JIS standard sieve whose mesh size was 850 µm and a JIS standard sieve whose mesh size was 200 µm, thereby obtaining a water absorbent resin (3), having an irregularly-pulverized shape, whose mass average particle diameter was 380

μm. In the water absorbent resin (3), a centrifuge retention capacity was 33.0 g/g and water soluble component was 8.0 mass %.

In 100 parts of thus obtained water absorbent resin (3), a surface cross-linking agent including 0.4 parts by mass of 1,4-butanediol, 0.6 parts by mass of propyleneglycol, and 2.7 parts by mass of pure water, was evenly mixed. The mixture was then heated at 210° C. for 40 minutes. Further, particles thereof were disintegrated so as to pass through a JIS standard sieve whose mesh size was 850 μm. Subsequently, the particles were subjected to the paint shaker test 1, thereby obtaining water absorbent resin particles (D) whose surfaces had been cross-linked.

Table 1 shows properties of the water absorbent resin particles (D).

Example 25

There was prepared an even mixture solution including 2 parts by mass of liquid aluminum sulfate 27 mass % solution for city water (product of ASADA KAGAKU KOGYO KABUSHIKIKAISHA), 0.4 parts by mass of 50% sodium lactate aqueous solution (product of Musashino Chemical Laboratory, Ltd.), and 0.02 parts by mass of propyleneglycol.

100 parts by mass of the water absorbent resin particles (D) and 0.488 parts by mass of the mixture solution were evenly mixed with each other, and the resultant was dried at 60° C. for one hour. The dried resultant was disintegrated so as to pass through a JIS standard sieve whose mesh size was 850 μm. Next, the particles were subjected to the paint shaker test 2. In this manner, a water absorbing agent (25) was obtained.

Table 1 shows properties of the water absorbing agent (25).

Comparative Example 5

The same operation was performed as Example 19 except that 0.02 parts by mass of 50% sodium lactate aqueous solution (product of Musashino Chemical Laboratory, Ltd.) was not mixed with 2 parts by mass of liquid aluminum sulfate 27 mass % solution for city water (product of ASADA KAGAKU KOGYO KABUSHIKIKAISHA) and 1 part by mass of liquid aluminum sulfate 27 mass % solution for city water (product of ASADA KAGAKU KOGYO KABUSHIKIKAISHA) was independently used. In this manner, a comparative water absorbing agent (5) was obtained.

Table 1 shows properties of the comparative water absorbing agent (5).

TABLE 1

| | CRC (g/g) | AAP (g/g) | SFC ($\times 10^{-7}$ cm$^3 \cdot$ s$\cdot$g$^{-1}$) | BR (mass %) | IBR (mass %) | ERM (mass %) |
|---|---|---|---|---|---|---|
| Water absorbent resin particles (A) | 26 | 24 | 64 | — | — | — |
| Water absorbent resin particles (B) | 31 | 26 | 26 | — | — | — |
| Water absorbent resin particles (C) | 29 | 25 | 51 | — | — | — |
| Water absorbing agent (1) | 25 | 22 | 127 | — | — | — |
| Water absorbing agent (2) | 25 | 22 | 152 | — | — | — |
| Water absorbing agent (3) | 25 | 22 | 145 | — | — | — |
| Water absorbing agent (4) | 25 | 22 | 163 | — | — | — |
| Water absorbing agent (5) | 25 | 22 | 115 | — | — | — |
| Water absorbing agent (6) | 25 | 22 | 124 | — | — | — |
| Water absorbing agent (7) | 25 | 22 | 166 | — | — | — |
| Water absorbing agent (8) | 25 | 23 | 115 | — | — | — |
| Water absorbing agent (9) | 25 | 21 | 167 | — | — | — |
| Water absorbing agent (10) | 25 | 22 | 142 | — | — | — |
| Water absorbing agent (11) | 25 | 22 | 136 | — | — | — |
| Water absorbing agent (12) | 25 | 22 | 115 | — | 6 | — |
| Water absorbing agent (13) | 25 | 22 | 140 | — | — | — |
| Water absorbing agent (14) | 25 | 23 | 130 | — | 4 | — |
| Water absorbing agent (15) | 25 | 22 | 125 | — | — | — |
| Water absorbing agent (16) | 25 | 22 | 138 | — | — | — |
| Water absorbing agent (17) | 26 | 24 | 129 | — | — | — |
| Water absorbing agent (18) | 26 | 23 | 130 | — | — | — |
| Water absorbing agent (19) | 30 | 23 | 50 | 0 | — | 20.0 |
| Water absorbing agent (20) | 29 | 23 | 125 | — | — | — |
| Comparative water absorbing agent (1) | 25 | 22 | 90 | — | 19 | — |
| Comparative water absorbing agent (2) | 30 | 23 | 40 | 15 | — | 2.8 |
| Comparative water absorbing agent (3) | 29 | 22 | 100 | — | — | — |
| Water absorbing agent (21) | 30 | 26*[1] | 5 | 0 | — | — |
| Comparative water absorbing agent (4) | 26 | 27*[1] | 65 | 90 | — | — |
| Water absorbing agent (22) | 31 | 24 | 47 | 2*[2] | — | 38.6 |
| Water absorbing agent (23) | 31 | 25 | 45 | — | — | — |
| Water absorbing agent (24) | 29 | 25 | 87 | — | — | — |
| Comparative water absorbing agent (5) | 30 | 23 | 33 | 83*[2] | — | 2.3 |
| Water absorbing agent (25) | 29 | 25 | 100 | — | — | — |
| Water absorbent resin particles (D) | 29 | 25 | 45 | — | — | — |

*[1] Measurement was performed with a load of 2.07 kPa (0.3 psi).
*[2] A blocking ratio obtained by leaving the resultant under conditions of 25° C. and 80 RH % for 60 minutes.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

According to the method of the present invention for producing a water absorbing agent, it is possible to suppress permeation of the metal components into the water absorbent resin particles and it is possible to make the metal components to evenly adhere to a vicinity of a whole surface of the water absorbent resin in a dot manner (the metal components locally exist). Thus, it is possible to realize high liquid permeability and even properties, and the water absorbing agent can be used as a water absorbing/retaining agent in various use. For example, it is possible to use the water absorbing agent in: absorbing article water absorbing/retaining agents such as a disposable diaper, a sanitary napkin, an incontinence pad, and a medical pad; agriculture/horticulture water retaining agents such as an alternative bog moss, a soil reforming/improving agent, a water retaining agent, and an agrichemical effect maintaining agent; architectural water retaining agents such as an interior wall condensation preventing agent, and a cement additive; a release control agent; a cold insulation agent; a disposable body warmer; a sewage coagulator; a food freshness maintaining agent; an ion exchange column material; a sludge or oil dehydrating agent; a desiccating agent; a humidity controlling agent; and the like. Further, the water absorbing agent obtained in the present invention is favorably used in an absorbing sanitary material, such as a disposable diaper and a sanitary napkin, which absorbs feces, urine, and blood.

The invention claimed is:

1. A water absorbing agent, comprising:
    water absorbent resin particles, including at least one of acrylic acid and a salt of acrylic acid as a base unit, whose surfaces have been cross-linked by performing a heating treatment or using an organic cross-linking agent;
    organic acid or a salt thereof; and
    water-soluble multivalent metal salt,
    wherein the water absorbing agent has an absorbency against pressure (AAP) so that the absorbency is 18 (g/g) or more against a pressure of 4.83 kPa.

2. The water absorbing agent as set forth in claim 1, wherein the organic acid or the salt thereof and the water-soluble multivalent metal salt locally exist in a vicinity of surfaces of the water absorbent resin particles.

3. The water absorbing agent as set forth in claim 1, comprising a multivalent metal component, wherein an extraction rate of the multivalent metal component ranges from 5.0 to 100.0 mass %.

4. The water absorbing agent as set forth in claim 1, wherein an amount of the water-soluble multivalent metal salt ranges from 0.001 to 10 parts by mass and an amount of the organic acid or the salt thereof ranges from 0.0001 to 5 parts by mass with respect to 100 parts by mass of the water absorbent resin particles.

5. The water absorbing agent as set forth in claim 1, further comprising a hydrophilic organic solvent.

6. The water absorbing agent as set forth in claim 1, wherein the organic acid or the salt thereof is alkali metal salt or ammonium salt.

7. The water absorbing agent as set forth in claim 1, wherein the organic acid or the salt thereof is a saturated organic acid or a salt thereof.

8. The water absorbing agent as set forth in claim 5, wherein an amount of the hydrophilic solvent is more than 0 and not more than 1 part by mass with respect to 100 parts by mass of the water absorbent resin particles.

9. The water absorbing agent as set forth in claim 1, wherein a centrifuge retention capacity (CRC) is 25 (g/g) or more and a saline flow conductivity is $30 \times 10^{-7}$ $cm^3 \cdot s \cdot g^{-1}$ or more.

10. The water absorbing agent as set forth in claim 2, comprising a multivalent metal component, wherein an extraction rate of the multivalent metal component ranges from 5.0 to 100.0 mass %.

11. The water absorbing agent as set forth in claim 2, wherein an amount of the water-soluble multivalent metal salt ranges from 0.001 to 10 parts by mass and an amount of the organic acid or the salt thereof ranges from 0.0001 to 5 parts by mass with respect to 100 parts by mass of the water absorbent resin particles.

12. The water absorbing agent as set forth in claim 2, further comprising a hydrophilic organic solvent.

* * * * *